(12) United States Patent
Goemann-Thoss et al.

(10) Patent No.: US 10,466,262 B2
(45) Date of Patent: Nov. 5, 2019

(54) LABORATORY INSTRUMENT WITH ACCESS CONTROL DEVICE AND METHOD FOR INSTRUMENT-CONTROLLED TREATMENT OF LABORATORY SAMPLES

(71) Applicant: Eppendorf AG, Hamburg (DE)

(72) Inventors: Wolfgang Goemann-Thoss, Hamburg (DE); Wolf Wente, Hamburg (DE); Andreas Thieme, Hamburg (DE); Jan-Gerd Frerichs, Norderstedt (DE); Christiane Markau, Hamburg (DE); Jan-Hendrik Hacker, Hamburg (DE)

( * ) Notice: Subject to any disclaimer, the term of this patent is extended or adjusted under 35 U.S.C. 154(b) by 0 days.

(21) Appl. No.: 14/508,703

(22) Filed: Oct. 7, 2014

(65) Prior Publication Data
US 2015/0125961 A1 May 7, 2015

(30) Foreign Application Priority Data
Oct. 7, 2013 (EP) ..................................... 13004812

(51) Int. Cl.
*G01N 35/00* (2006.01)
(52) U.S. Cl.
CPC .................. *G01N 35/00871* (2013.01); *G01N 2035/0091* (2013.01); *G01N 2035/00881* (2013.01); *Y10T 436/11* (2015.01)
(58) Field of Classification Search
CPC ....... G01N 35/00871; G01N 35/00722; G01N 2035/00881; G01N 2035/0091; G01N 2035/00891; Y10T 436/11
(Continued)

(56) References Cited

U.S. PATENT DOCUMENTS 6,544,476 B1 4/2003 Mimura et al.
7,593,787 B2 * 9/2009 Feingold ............ G01N 35/0092
700/245
(Continued)

FOREIGN PATENT DOCUMENTS

DE  10 2011 109 332 A1 * 2/2013 ................ B01L 7/00
EP        0952452 A1   10/1999
(Continued)

OTHER PUBLICATIONS

Merriam-Webster.com, Integrated Definition, obtained on Mar. 15, 2018, p. 1-9. (Year: 2018).*
(Continued)

*Primary Examiner* — Christine T Mui
(74) *Attorney, Agent, or Firm* — Todd A. Lorenz

(57) ABSTRACT

The invention relates to an access control device for a laboratory instrument serving for the instrument-controlled treatment of a laboratory sample and this laboratory instrument, and also to a method for controlling the access to functions of the laboratory instrument by means of the access control device, wherein the access control device comprises: a first interface apparatus and a second interface apparatus; and a control apparatus wherein the control apparatus is configured: a) to establish one or more first data connections to one or more user interface apparatuses via the first interface apparatus; b) to establish a second data connection to the laboratory instrument via the second interface apparatus; and c) to control authorizations and/or access permissions for user access to functions of the laboratory instrument via the first and second data connections.

14 Claims, 4 Drawing Sheets

(58) Field of Classification Search
USPC .................................. 436/43; 422/67, 63, 50
See application file for complete search history.

(56) References Cited

U.S. PATENT DOCUMENTS

| | | |
|---|---|---|
| 2002/0032762 A1 | 3/2002 | Price et al. |
| 2002/0135678 A1* | 9/2002 | Bacus .................... G01N 1/312 348/143 |
| 2003/0141116 A1 | 7/2003 | Nuesch et al. |
| 2004/0171171 A1 | 9/2004 | Appoldt et al. |
| 2005/0014285 A1 | 1/2005 | Miller |
| 2005/0112542 A1 | 5/2005 | West |
| 2005/0131734 A1 | 6/2005 | Sugiyama |
| 2005/0159982 A1 | 7/2005 | Showalter et al. |
| 2005/0192908 A1 | 9/2005 | Jorimann et al. |
| 2006/0173575 A1 | 8/2006 | Lefebvre et al. |
| 2006/0242276 A1* | 10/2006 | Price et al. .................... 709/220 |
| 2007/0143465 A1 | 6/2007 | Gonzalez et al. |
| 2007/0233303 A1 | 10/2007 | Naito et al. |
| 2007/0255756 A1 | 11/2007 | Satomura et al. |
| 2008/0059472 A1 | 3/2008 | Yamamoto et al. |
| 2008/0256227 A1 | 10/2008 | Malin |
| 2010/0106427 A1 | 4/2010 | Fukuma et al. |
| 2010/0271479 A1 | 10/2010 | Heydlauf |
| 2011/0246215 A1 | 10/2011 | Postma et al. |
| 2013/0045473 A1* | 2/2013 | Duerr .................. B01F 11/0014 435/3 |
| 2013/0159135 A1 | 6/2013 | Jones et al. |

FOREIGN PATENT DOCUMENTS

| | | |
|---|---|---|
| EP | 0973115 A2 | 1/2000 |
| EP | 1248170 A1 | 10/2002 |
| EP | 1840576 A2 | 10/2007 |
| EP | 1981245 A1 | 10/2008 |
| EP | 2182364 A2 | 5/2010 |
| EP | 2182365 A2 | 5/2010 |
| EP | 2299277 A1 | 3/2011 |
| EP | 2450711 A1 | 5/2012 |
| WO | WO 1994011838 A1 | 5/1994 |
| WO | WO 2008012104 A2 | 1/2008 |
| WO | WO 2009/085534 * 7/2009 .......... G01N 33/543 |
| WO | WO 2009085534 A1 | 7/2009 |
| WO | WO 2012/045415 A1 | 4/2012 |

OTHER PUBLICATIONS

U.S. Appl. No. 14/508,716 (U.S. Publication No. US 2015-0104796 A1), entitled, "System comprising at least two laboratory instruments for instrument-controlled handling of a partial problem in a treatment process containing treatments of at least one laboratory sample, laboratory instrument and method," filed Oct. 7, 2014, of Goemann-Thoss, et al.

U.S. Appl. No. 14/508,722 (U.S. Publication No. US 2015-0105877 A1), entitled, "Configuration control device for a laboratory instrument, laboratory instrument with the configuration control device for instrument-controlled treatment of at least one laboratory sample and a method for configuring the laboratory instrument by means of the configuration control device," filed Oct. 7, 2014, of Goemann-Thoss, et al.

U.S. Appl. No. 14/508,724 (U.S. Publication No. US 2015-0127270 A1), entitled, "Laboratory instrument, system and method for instrument-controlled treatment of at least one laboratory sample using at least one consumable," filed Oct. 7, 2014, of Goemann-Thoss, et al.

* cited by examiner

LABORATORY INSTRUMENT WITH ACCESS CONTROL DEVICE AND METHOD FOR INSTRUMENT-CONTROLLED TREATMENT OF LABORATORY SAMPLES

The invention relates to an access control device for a laboratory instrument, a laboratory instrument with an access control device for instrument-controlled treatment of at least one laboratory sample and a method for controlling the access by means of the access control device.

Such laboratory instruments are used in chemical, biological, biochemical, medical or forensic laboratories to handle laboratory samples, in particular liquid laboratory samples, with great efficiency. Such laboratory instruments at least partly automate treatment steps which would otherwise have to be performed manually and thus increase the speed, precision and reliability of these treatments. A treatment of laboratory samples, which are usually in liquid form, may be directed to modifying or examining these laboratory samples, in particular the composition thereof, in a physical, chemical, biochemical or other manner.

The aforementioned laboratory instruments comprise one or more treatment apparatus(es) for instrument-controlled treatment of the at least one laboratory sample. They often have a program control, by means of which a user of the laboratory instrument can set the treatment to be performed by setting the desired program parameters. The program parameters are set by means of an operating unit of the laboratory instrument, which enables the input and output of information, in particular of values of the program parameters. The operating unit is released for access by the user when the laboratory instrument is not performing a treatment. By contrast, if an instrument-controlled treatment is being carried out in the laboratory instrument, the operating unit is not, for safety reasons, released for user access without query or confirmation so as not to endanger the safe progress of the treatment. The treatment is performed in at least partly automated fashion. After the treatment has been completed, the user can continue to use the treated sample and the laboratory instrument is available for a further use. The subsequent user of the known laboratory instrument will once again enter the desired settings of the program parameters which can be set for the subsequent treatment, start the treatment and remove the treated sample after treatment has been completed and make the laboratory instrument available for further use. In order to increase the productivity of a laboratory, there is the option of equipping a laboratory with a plurality of laboratory instruments of the same type. Going beyond such known approaches, the present invention uses a novel configuration of laboratory instruments in order to increase further the productivity of a laboratory.

It is an object of the present invention to make available an access control device for a laboratory instrument, the laboratory instrument with an access control device, and a method for instrument-controlled treatment of at least one laboratory sample, by means of which the productivity in a laboratory can be improved.

The invention achieves this object by means of, in particular, the access control devices, the laboratory instruments and the methods described herein. Preferred embodiments of the invention are, in particular, the subject matter of the dependent claims.

In a laboratory instrument, the access control device according to the invention enables the access of one or more further users to the laboratory instrument to be controlled when a first user is already logged on and the session of said first user is still running on the laboratory instrument, i.e. when the further user(s) attempt access. As a result of this embodiment, the laboratory instrument can be used more efficiently and the productivity of the laboratory can be improved.

Preferred embodiments of the access control device and of the laboratory instrument with this access control device are mentioned within the description of the present invention or can be gathered therefrom.

The access control device is preferably configured to control the request of the at least one further user in respect of logging onto the access control device, in particular to control the access to at least one function of the laboratory instrument, in particular to grant the request (access granted) or to reject the request (access denied), during the session of the first user.

The access control device is an apparatus configured for data processing. It serves for access control. The access control device comprises a control apparatus. The control apparatus is embodied for data processing. In particular, the control apparatus is an electronic control apparatus. It preferably has a data processing apparatus which, in particular, is electronic.

Within the scope of the present invention, a control apparatus generally comprises, in particular, a data processing apparatus, in particular a computer unit (CPU) for processing data and/or a microprocessor, or said control apparatus is a data processing apparatus. A computer unit of the control apparatus of a laboratory instrument is preferably also configured for controlling the treatment process and/or the individual treatments.

The term "treatment" means, in particular, that a laboratory sample, which is usually in liquid form, is moved and/or transported and/or examined and/or modified, in particular modified physically, chemically, biochemically or in another way in terms of the composition thereof.

The control apparatus of the laboratory instrument and/or the access control and/or the optional user interface apparatus—in particular all of these—can be integrated in a physical instrument unit but can also in each case be independent physical instrument units. A physical instrument unit can, in particular, be a module which is or can be connected to the laboratory instrument. The control apparatus of the laboratory instrument and/or the access control device and/or the optional user interface apparatus or components of these components can also be implemented by software functions or can, in particular, be available as program code. By way of example, a laboratory instrument can comprise a computer which, in combination with software functions, in each case at least partly implements the control apparatus of the laboratory instrument and/or the optional access control device and/or the optional user interface apparatus. By way of example, if the access control device is integrated into the laboratory instrument, the access control device itself may be part of the control apparatus of the laboratory instrument or be implemented by means of the control apparatus, in particular by software functions, in particular at least partly as executable program code.

A module can, in particular, comprise the access control device and/or a user interface apparatus. A module is an instrument which is separate from other instruments and/or an instrument which can be separated from the other instrument, in particular the laboratory instrument. A laboratory instrument may comprise a connection apparatus, by means of which the module can be connected to the laboratory instrument, in particular by means of a connection which is detachable by the user. A module may be portable, i.e.

transportable by a user. The module can also be securely connected to the laboratory instrument. The modular design offers advantages during the production of laboratory instruments. A portable module offers greater flexibility when using a laboratory instrument.

A communication apparatus is preferably configured for the transmission and/or reception of data, in particular for the data interchange via a data connection provided by the communication apparatus, in particular for a remote data connection to a remote instrument. In particular, the instrument arranged at a distance from a laboratory instrument is also referred to as "remote instrument" or external instrument. In particular, a data processing apparatus which is not a component of a laboratory instrument is also referred to as an external data processing apparatus. The data connection, in particular the remote data connection, can be established over a restricted network of computers (in particular an intranet) or over a worldwide network of computers (in particular the Internet). The data connection, in particular the remote data connection, can also be established over a wireless connection. The data connection, in particular the remote data connection, can, in particular, be established over a mobile communications connection.

A data connection connects, in particular, two data-processing units, in particular two data-processing apparatuses, in such a way that data can be interchanged, either unidirectionally or bidirectionally, between the units. The data connection can be realized with or without cables, in particular as a wireless connection. A remote data connection connects, in particular, two data-processing units, in particular two data-processing apparatuses, which are arranged at a distance from one another, which are therefore, in particular, not components of the same instrument, in particular of the same access control device, user interface apparatus or of the same laboratory instrument if the aforementioned instruments are embodied as separate instruments. A data connection, in particular a remote data connection, from one instrument to another instrument is preferably realized by a direct connection between the two instruments or by means of an indirect connection between the two instruments such that a third instrument is switched between the two instruments in order to forward the data. In particular, a remote data connection can be realized via a network of computers, in the case of which the instruments connected via the remote data connection are connected via the network. The network can be a restricted network, e.g. an intranet, or a world-wide network, in particular the Internet.

The data processing apparatus preferably comprises a computer unit, in particular a CPU, furthermore preferably at least one data storage apparatus, in particular for volatile and/or permanent storage of data. The data processing apparatus is preferably embodied to establish one or more first data connections to one or more user interface apparatuses via the first interface apparatus, which, in particular, may be components of the access control device or of the laboratory instrument; preferably to establish a second data connection to the laboratory instrument via the second interface apparatus; and preferably to control access permissions for the access of users via the user interface apparatuses and the first and second data connections to functions of the laboratory instrument; wherein, preferably, the access permissions can be controlled in such a way that simultaneous access (being logged in) of a first and at least one further user occurs with in each case separately assigned access permissions to functions of the laboratory instrument.

An interface apparatus serves for connecting two apparatuses which can each process, in particular transmit and/or receive, signals, in particular information, in particular data. An interface apparatus can contain at least one hardware interface and/or at least one software interface.

Hardware interfaces are, in particular, interfaces between electrically operating units in accordance with the usual understanding in electrical engineering and electronics. Presently, the phrase "hardware interface" in particular also denotes the connection components between at least two electrically operating units themselves, i.e., in particular, all constituents which enable this connection, e.g. integrated circuits, electronics and lines, by means of which electrical signals are transmitted between the at least two electrically operating units. In particular, these two electrically operating units can be a laboratory instrument and an external data processing apparatus or two laboratory instruments or two electrically operating units within a laboratory instrument. A hardware interface need not, but can, comprise a detachable connection apparatus for releasing and/or re-establishing this connection, in particular at least one connector.

Software interfaces, in particular software-side data interfaces, are, in particular, logical connection points in an information management system, in particular a software system: they enable and regulate the interchange of commands and data between various processes and components. Software interfaces may be data-oriented interfaces used for communication purposes only. In this case, the software interface merely contains information which is interchanged between involved system parts.

The access control device is preferably configured to control the access permissions by virtue of the control apparatus using a data connection to a database for access permissions. The database for access permissions is preferably stored in at least one, preferably in exactly one, storage apparatus for access permissions. The at least one storage apparatus for access permissions can be disposed in the access control device and/or it can be disposed in an external data processing apparatus. "External" means that the instrument, in this case the data processing apparatus, is not a constituent of the device in question, in this case the access control device. The database for access permissions can be stored centrally, but it can also be stored in a plurality of storage apparatuses which can each have some of the data in the database or else have a copy of the data in the database.

An—in particular external—data processing apparatus can be a computer, in particular a server, which is configured in particular for establishing a data connection to more than one access control device and/or to more than one laboratory instrument. An—in particular external—data processing apparatus can have a computer or microprocessor or can be a computer or microprocessor. A server is, in particular, a computer, the hardware of which is preferably tuned to server applications. An external data processing apparatus can be a mobile data processing apparatus, which is configured for establishing a wireless data connection, in particular a data connection via a restricted computer network, in particular an intranet, or a world-wide computer network, in particular the Internet. A computer network is a combination of various technical, primarily independent, electronic systems (in particular computers, but also sensors, actuators, agents and/or other radio components, etc.), which combination enables the communication between the individual systems.

The access control device can comprise a communication apparatus for establishing a data connection to an external data processing apparatus, in particular via the first, second or another interface apparatus of the access control device. The access control device is preferably embodied to establish the access permissions using the data connection to the external data processing apparatus, in particular via the first, second or another interface apparatus of the access control device. The external data processing apparatus preferably comprises at least part, or all of, the database for access permissions.

The control apparatus of the access control device is configured to control authorizations and/or access permissions for the access of users via the user interface apparatuses and the first and second data connections to functions of the laboratory instrument. As a result of this, a user-dependent use of the laboratory instrument is possible, which is controlled depending on the respectively allocated access permissions. In particular, simultaneous use of the laboratory instrument by at least a first and at least a second user is made possible.

The access control device performs the access control. The phrase "access control" denotes, in particular, methods for managing the requests for resources and/or data, which are managed by an information management system and which are handled for managing the decisions as to how the request is handled, in particular whether or not access is granted and/or in what manner the access is or is not granted. In particular, the information management system can be an operating system which is executed on the access control device. If the user of an information management system wishes to perform a specific operation on a specific resource and/or on specific data, the access control device makes a decision as to whether this request should in actual fact be granted or whether it should be denied. An access control decision (yes/no) relates to, in particular, an access control triple consisting of "subject", "object" and "operation".

In particular, an active entity of a system, wishing to perform a specific operation on a specific object, is referred to as a subject. In this context, an entity denotes a uniquely determinable unit, relating to which information is to be stored and/or processed. The unit may be material or immaterial, concrete or abstract. Subjects are, in particular, human users of an information management system or computer programs which are used by human users for completing tasks. A subject may also be a group of users, e.g. laboratory worker, servicing technician, administrator. Accordingly, the group combines a plurality of individual subjects.

A user may represent an individual or a group of a plurality of individuals or a class of individuals, which were selected in accordance with a class rule or role rule.

The access control device can preferably distinguish between the at least one first user and the at least one second user. A user is preferably uniquely identified by the access control device. To this end, the access control device preferably processes identification data. The access control device is preferably embodied to authenticate the requesting user, i.e. to perform a verification method, by means of which the authenticity of the requesting user is checked and the user is authenticated if the verification is positive. By way of example, authentication data contain a login text and a password text or a data set for facial recognition or for an iris scan or for a fingerprint scan, etc. Furthermore, authentication can be performed by means of an RFID chip or NFC chip or via gesture identification. In particular, an authentication may be performed in situ by means of direct access to the laboratory instrument or the access control device thereof, or by means of remote access.

The access control device preferably comprises an information management system, by means of which the access control is realized. The information management system is preferably an operating system of a laboratory instrument and/or an operating system of the access control device of a laboratory instrument, by means of which the access control device and/or the laboratory instrument are operated.

The access control device is preferably embodied to log the requesting user, in particular a plurality of requesting users, in particular the at least one first user and the at least one second user, onto the access control device, in particular onto the information management system of the access control device. The log-on process is also referred to as logging in. The successfully logged-on user preferably receives predetermined authorizations and/or access permissions. The user himself can cancel being logged on or this can be cancelled by other conditions, for example by the instrument-controlled logging off of the user, in particular if a maximum logged-on time, during which the user was logged in, without interruption, via the access control device is exceeded or after a predetermined time of inactivity or depending on the time of the end of a treatment performed by the user or due to individual process programming. Cancelling of logging on preferably means that the authorization granted during the log-on is revoked.

Logging into the information management system is preferably brought about by virtue of the user being authenticated. After authentication, the user obtains, for logging-in purposes, a personalized access to the information management system, with authorizations and/or access permissions, which are established by means of the database for access permissions. A session starts with the login and it is terminated by logging out, which is also referred to as logging off.

The access control device is preferably embodied to release the use of, i.e. authorize the authenticated user to use, the authorizations, operations and objects on the laboratory instrument or the functions and services of the laboratory instrument, which comprises the access control device, as a function of the predetermined access permissions. The access control device is preferably software controlled, in particular program controlled. LDAP (Lightweight Directory Access Protocol) is preferably used as application protocol when implementing the software functions.

During access or attempted access, an object refers to, in particular, a passive entity on which an operation is to be performed. Objects are also referred to as "resources". Objects may be e.g.: data or data collections, i.e. files, data objects in databases, e.g. tables or columns, services or functions, in particular those services or functions which can be performed by the access control device and/or the laboratory instrument. By way of example, such services may denote the making available of a calendar database, wherein this use may provide the display of calendar dates, the read permissions and/or write permissions on the calendar database. By way of example, such services and functions may denote a notification function, by means of which it is possible to send notifications to the users, which notifications may, in particular, contain information about the availability of the laboratory instrument during a specific calendar time period. In particular, making it possible for treatment to be performed, which, in particular, may contain the granting of the access permissions required for this, would also be such a function. By way of example, a function may be the switching-on of the UV illumination of the laboratory instrument or the opening of a housing door of a laboratory instrument housing.

Processes carried out on an object are referred to as operations. In particular, operations can be functions, in particular functions of the access control device or of the laboratory instrument. A plurality of functions can be performed on one object. If the object is a file, possible operations are writing, reading, adding, modifying, copying or deleting data. If the object is a service or a function, performing may be the only possible operation. The number of possible operations depends on the type of the object. The number of operations which can be performed by individual subjects on the same object may differ.

A specific object in combination with a specific operation is, in particular, referred to as an authorization. By way of example, a "read authorization" can be understood to be the combination of the operation "read" with the object "file", while e.g. an "execution authorization" can be understood to be the operation "execute" with the object "function".

In particular, the access control can be formulated as a permission function, formally described by permission_for(subject, object, operation)→(yes, no)

If this function is applied to the triple of parameters (subject, object, operation), the permission function returns either "yes" (access granted) or "no" (access denied).

In this permission function, it is also possible to provide a further input parameter which supplies a further condition for the access decision. By way of example, this condition can denote the purpose for which a specific access should take place. Furthermore, it is possible that the permission function returns not—or not only—the yes/no decision about the access permission, but also a condition (also referred to as "obligation"), as a function of which a decision is made about the access permission. In particular, this allows "permission with conditions" to be defined. In particular, such an obligation is already satisfied before the access or access attempt, but may also be satisfied during— or after—the access or the operation to be permitted.

The access control can take place in accordance with one or more specific data models. One such specific data model is, in particular, the access control model (ACM). In particular, the access control may comprise a so-called reference monitor. In particular, this component should be understood to be the functional core of the access control device. The reference monitor fulfils the function of deciding whether the access to an object, as desired by a subject, is granted. The access control device may preferably not release any access to a resource of the laboratory instrument without the reference monitor being used. The reference monitor preferably also satisfies the function of recording access attempts that took place.

The database about access permissions preferably contains information in the form of data about which operations are available for an object, in particular as a function of a specific time or time period. In particular, this renders it possible to set whether the access to the at least one treatment apparatus is granted to a user at a specific time and/or during a specific period of time, in particular whether the permission for starting or modifying a treatment on the laboratory instrument has been allocated at a specific time and/or in a specific time period, wherein the laboratory instrument is and/or can be connected to the access control device by means of the second data connection.

The database about access permissions preferably contains information in the form of data relating to which authorizations can be allocated to the requesting user, in particular as a function of possible permissions due to belonging to a group and/or belonging to a role.

The access control is preferably configured in accordance with one, or else in accordance with more, of the known basic forms DAC ("Discretionary Access Control"), MAC ("Mandatory Access Control") or RBAC ("Role-Based Access Control"), with RBAC being particularly preferred.

The DAC model is also referred to as identity-based access control. The identity of the requesting user is evaluated in order to determine which permissions the user may obtain and/or which permissions are assigned to said user. If the access control device is at least partly embodied in accordance with the DAC model, then it is possible that an object created by the user is always provided with specific permissions, in particular read and/or write permissions. Then, the creating user is the owner thereof, at least after the object has been created. By way of example, such an object to be created may be a file, which represents a process program or a set of parameters, in particular program parameters. It is possible and preferred for the access control device to be embodied in such a way that the owner of an object can allocate permissions to at least one further user, in particular permissions in relation to an operation on the object, e.g. the permission to execute a process program. It is possible and preferred for the access control device to be embodied in such a way that the owner of an object may transfer ownership to a new owner or a co-owner. By way of example, a first user could grant a second user the permission to have the same permissions as the first user over a process program created by the first user. In particular, DAC may be configured as so-called liberal DAC (owner may transfer the owner permissions) or strict DAC (owner may not transfer the owner permissions). In the case of liberal DAC, there can be provision, in particular, for a restriction in the number of permission transfers, e.g. as one level grant, two level grant or multilevel grant.

The access control device may, particularly in accordance with a DAC-ACM model, comprise an access matrix. The access matrix is a data table in which each line represents a subject and each column represents an object. This data table is preferably contained in the database for access permissions. In each field, the access matrix may contain at least one further data record, by means of which the permissions in this field are differentiated on the basis of a further condition, in particular in accordance with a role of the user. Each subject/object pair, i.e. element, in the access matrix contains information about the permissible operations which the subject may undertake on the object. The element may also display information about the ownership of the object. In particular, an access matrix may be stored as an access control list, in which there is a list for each object specifying what subject has what permissions on the object. An access matrix may also comprise capability lists, in which what operations may be carried out on what objects is stored for the subjects in the access matrix. A capability list may form a certificate for a user. This is expedient, particularly if the user should be awarded a certificate which temporarily or permanently assigns him specific permissions on the laboratory instrument. The certificate is preferably used in order to qualify the user, in particular after the user has gone through a qualification method on the laboratory instrument or on an external data processing apparatus. The access matrix may further comprise authorization tables, in which tuples of subject, object and operation are contained. The access matrix can preferably be modified by the access control device.

The RBAC model provides for individual subjects not to be assigned permissions directly, but rather indirectly by means of so-called "roles". A possible standard of the RBAC model, which can be applied within the scope of designing the access control device, is described in detail in US standard ANSI INCITS 359-2004. The access control device may be embodied at least partly as a RBAC model, in particular at least partly in accordance with the aforementioned US standard.

Preferably, the access control provides the use of at least one role, preferably of a plurality of roles, wherein, in particular, permissions are in each case combined within the role. The at least one role is preferably stored in the database for access permissions. In particular, a role is suitably adapted to a responsibility or a problem description within the scope of using a laboratory instrument, in particular within the business using the laboratory instrument and/or in the business which fulfils a servicing contract relating to the laboratory instrument by virtue of e.g. performing diagnostic functions on the laboratory instrument, and/or in the manufacturer of the laboratory instrument, which e.g. transmits firmware updates, calibrations or information about the laboratory instrument and/or the accessories thereof directly to the laboratory instrument via the access control device. In particular, such roles can combine permissions. Instead of storing a set of individual rights for each user, the latter can be assigned at least one role. The role assignment is particularly reliable in terms of the implementation and requires relatively little outlay, in particular management outlay when establishing and storing permissions.

The access control preferably provides for at least two, preferably a plurality of, roles. Possible roles are, in particular, administrator ("Admin"), maintenance, normal laboratory user ("LabUser"), inexperienced laboratory user ("Inexperienced"), manager. Such roles enable a secure and efficient access control. The use of a laboratory instrument provided with the access control device is safe and efficient. This prevents, in a simple manner, a user, for example due to lack of qualification, from performing certain operations on the laboratory instrument which could possibly lead to damage or inefficient use of the laboratory instrument or to increased costs during operation, e.g. due to excessive use of consumables used for a treatment.

The access control preferably provides at least one role, or more than one role, which can be assigned simultaneously to a user. Therefore, an individual can, for example, obtain access as administrator or as normal laboratory user, depending on a further condition. The user can preferably decide himself the role in which he obtains access to the laboratory instrument. However, it is also possible that the user does not decide this himself, but that this is decided by the access control device. This condition may be the data record used for authentication purposes, in particular the used password, or it may depend on a parameter of the laboratory instrument, in particular on an operating parameter of the laboratory instrument, e.g. an operating parameter which characterizes an error state of the laboratory instrument.

In particular, the RBAC model has four components: "core RBAC" contains the basic permission structure, upon which the other components are built. "Core RBAC" consists, in particular, of the following five data elements: user, roles, objects, operations and authorizations. "Hierarchical RBAC" extends the roles described in "core RBAC" by an inheritance hierarchy. Inheriting means that a manager can additionally be assigned e.g. all permissions of a normal laboratory user. "Static separation of duty" may contain information about a user never being allowed to be assigned certain roles at the same time. "Dynamic separation of duty" may contain information about a user never being allowed to use certain roles simultaneously within a session.

The aforementioned preferred embodiments of a laboratory instrument according to the invention also apply to a laboratory instrument which is a component of the system according to the invention.

The control apparatus of the access control device is preferably configured to allow more than one user to be logged on simultaneously on the access control device in order to have authorizations and/or access permissions assigned to them. Such an access control device for simultaneous use of a laboratory instrument constitutes an efficient solution for increasing the productivity in a laboratory.

Preferably, in a first preferred design of the access control device, the access control device or the control apparatus of the access control device is configured, during the session of the user, in particular the first user, also to log at least one further requesting user, in particular a second requesting user, onto the access control device and to start a session, in particular for this further user, said session occurring parallel to the session of the first user for at least some of the time. In any case, provision is preferably made in the case of logging the user onto the access control device, i.e. in the case of successful authentication, for the at least one further requesting user, in particular second requesting user, to be assigned authorizations and/or access rights during the session of the (first) user.

The phrases "first user" and "second user" denote the circumstance that the first user was logged on temporally before the log-on attempt of the second user. In any case, in the event of a successful log-on attempt of the second user, the latter is likewise logged on, to be precise still during the session of the first user. There may be further users logged on the access control device, which, temporally, were logged on before the first or the second user or after they logged off. After logging on, the first user is preferably assigned first authorizations and/or first access permissions, preferably in accordance with a first permission profile or first certificate. During the log on, the second user is preferably assigned second authorizations and/or second access permissions, preferably in accordance with a second permission profile or second certificate. The first and second access permissions preferably differ from one another, the first and second authorizations preferably differ from one another, the first and second permission profiles or certificates preferably differ from one another. However, the access permissions and authorizations of different users may also be at least partly identical.

Every user can establish a first data connection with the access control device by means of the same user interface apparatus or a plurality of users can establish a first data connection with the access control device by means of different user interface apparatuses. A user interface apparatus can be a component of the access control device. An access control device can be a component of the user interface apparatus. A user interface apparatus can be a component of a laboratory instrument. A user interface apparatus preferably comprises in each case: a control apparatus for a user interface apparatus; a communication apparatus for establishing a data connection to a laboratory instrument by means of an interface apparatus of same; an input apparatus for acquiring user inputs of a user; an output apparatus, in particular an indication unit and/or a display, for outputting information to the user. Here, the control apparatus of the user interface apparatus is preferably configured to interchange data with the laboratory instrument via the data connection, which data were obtained from the user inputs and, in the laboratory instrument according to the invention, cause the second user to be granted authorizations and/or access permissions on the laboratory instrument according to the invention such that a simultaneous log on and/or the simultaneous access of a first and at least a second user on the laboratory instrument according to the invention with respectively assigned access permissions to functions of the laboratory instrument can be controlled via the interface apparatus.

The access control device can be a component of the laboratory instrument for which the access control device controls the authorizations and/or access rights. In particular, the access control device can be a part of the control apparatus of the laboratory instrument, for example by virtue of e.g. at least partly being embodied as program code of a microprocessor-based control apparatus of the laboratory instrument. However, it can also be provided separately from this laboratory instrument and can, in particular, be a module which can be connected to said laboratory instrument. In particular, this access control device can be a mobile instrument, i.e. it can, in particular, be transportable by a human.

Preferably, in a second preferred configuration of the access control device which, in particular, may comprise the first configuration, the access control device or the control apparatus of the access control device is configured to assign, in any case after the at least one further requesting user has logged on, authorizations and/or access permissions to said at least one further requesting user during the session of the first user.

Preferably, in a third preferred configuration of the access control device which, in particular, may comprise the first or the second configuration, the access control device or the control apparatus of the access control device is configured in such a way that the access permissions and/or authorizations can be controlled in such a way, i.e., in particular, granted or denied, that there can be simultaneous access by a first and at least one further user with in each case separately assigned access permissions to functions of the laboratory instrument. The control apparatus of the access control device is configured to control access permissions in such a way that at least a first user obtains at least first access permissions and at least a second user obtains at least second access permissions, wherein, in particular, the at least first and the at least second access permissions may differ. In particular, the control apparatus of the access control device is configured to be able to allocate user-dependent access permissions simultaneously to a plurality (N=2-10) or multiplicity (N>10) of users. As a result, the use of a laboratory instrument provided with this access control device becomes particularly efficient.

The access control device, in particular the control apparatus of the access control device, is preferably configured so that the access permissions are controlled in such a way that there can be simultaneous access by a first and at least one further user with in each case separately assigned access permissions to functions of the laboratory instrument and, in particular, this also occurs in the case of simultaneous log on of the users to the access control device.

Preferably, in a fourth preferred configuration of the access control device which, in particular, may comprise the first, second or third configuration, the access control device or the control apparatus of the access control device can be configured in such a way that, when a first user has activated one or more functions of the laboratory instrument, the authorizations and/or access permissions of each further logged-in user are set in such a way that the performance of an already activated function of the laboratory instrument cannot be influenced by an activation of a function permitted in accordance with the authorizations and/or access permissions of the further user. The function activated by the first user may, for example, be that a treatment was started, which, in particular, is being carried out at the time at which the second user activates a second function. The activation of the second function is only permitted if this second function does not disturb the first function. This renders it possible to prevent the activity of the first user being disturbed by inputs of the second user.

Preferably, the access control device, in particular the control apparatus of the access control device, is configured in such a way that, if a first user is logged on, the access permissions of every further logged-on user are set as a function of the authorizations and/or access permissions of the first user in such a way that an activation of a function of the laboratory instrument, permissible in accordance with the authorizations and/or access permissions of the further user, cannot influence a potential execution of the function of the laboratory instrument, permissible in accordance with the authorizations and/or access permissions of the first user. As a result, it is possible, already on the basis of the log-on data and/or the time of the log ons, to set and ensure that the authorizations and/or access permissions assigned to the two users in each case do not lead to a one-sided or mutual disturbance of the functions of the laboratory instrument activated by the users and, in particular, do not lead to disturbance of an active, i.e. progressing, treatment.

Preferably, in a fifth preferred configuration of the access control device which, in particular, may comprise the first, second, third or fourth configuration, the access control device or the control apparatus of the access control device is configured to allow, when at least one condition is present, an amendment of the authorizations and/or access permissions in such a way that a further user at least partially obtains the authorizations and/or access permissions of the first user instead of said first user. By way of example, this condition may be that the further user has a higher rank, in particular if an administrator requires access to the laboratory instrument for administrative reasons. The condition may also be that the first user has permitted the second user to at least partly or completely override the authorizations and/or access permissions in the aforementioned manner, e.g. by changing a parameter of the access control device or of the laboratory instrument. In particular, this condition can assume that a notification was sent to the further user by means of a communication apparatus, which notification enables the further user to at least partly obtain the aforementioned authorizations and/or access permissions. To this end, in particular, the access control device, and/or the laboratory instrument, and in particular the user interface apparatus or the external data processing system of the further user comprises a communication apparatus. In this manner, the access to the functions of the laboratory instrument can be configured more flexibly.

Preferably, in a sixth preferred configuration of the access control device which, in particular, may comprise the fifth configuration, the access control device or the control apparatus of the access control device is configured in such a way that the authorizations and/or access permissions obtained by the further user instead of the first user contain the permission for controlling the treatment apparatus. As a result, the distribution of the "treatment apparatus" resource is configured flexibly.

Preferably, the access control device, in particular the control apparatus of the access control device, is configured in such a way that the authorization for controlling the treatment apparatus is only allocated to a single user, particularly within a predetermined period of time. This authorization characterizes, in particular, starting, modifying or changing of a treatment. This furthermore ensures that a situation, in which the running treatment is inadvertently modified or stopped by a further user, cannot occur.

Preferably, in a seventh preferred configuration of the access control device which, in particular, may comprise the sixth configuration, the access control device or the control apparatus of the access control device is configured in such a way that the function performed in accordance with the authorizations and/or access permissions of the first user contains the treatment of the at least one sample by the treatment apparatus. This furthermore ensures that a situation, in which the running treatment is inadvertently modified or stopped by a further user, cannot occur.

Preferably, in an eighth preferred configuration of the access control device which, in particular, may comprise the first, second, third, fourth, fifth, sixth or seventh configuration, the access control device or the control apparatus of the access control device is configured in such a way that the authorizations and/or access permissions of the first user or of each further user are set as a function of the operating state of the laboratory instrument. This enables an even more flexible use of the laboratory instrument.

The first interface apparatus preferably enables logging on and accessing functions of the laboratory instrument via at least two different user interface apparatuses.

Preferably, in a ninth preferred configuration of the access control device which, in particular, may comprise the first, second, third, fourth, fifth, sixth, seventh or eighth configuration, the access control device or the control apparatus of the access control device is configured in such a way that, in the case of logging on via a second user interface apparatus, a check is carried out as to whether the logging-on user has already in advance, via a first user interface apparatus,
 a) activated one or more of the currently performed functions of the laboratory instrument or
 b) is already logged on, and,
if condition a) or b) is satisfied, the authorizations and/or access permissions assigned to the user during the preceding log on by the access control device via the first user interface apparatus are assigned for access to the laboratory instrument via the second user interface apparatus. In this manner, the user can use a laboratory instrument by means of a plurality of user interface apparatuses; in particular, he can change the user interface apparatus without needing to interrupt the use of the laboratory instrument. This can be helpful, in particular, in order to control or observe a progressing treatment from different locations or in order to continue the programming of a process program from different locations. In particular, a user could leave the laboratory and continue to control and/or observe the use of the laboratory instrument from a mobile user interface apparatus.

Preferably, in a tenth preferred configuration of the access control device which, in particular, may comprise the ninth configuration, the access control device or the control apparatus of the access control device is configured in such a way that, in particular in addition to conditions a) or b), a check is carried out as to whether at least one further predetermined condition is satisfied during the log on at the second user interface apparatus and the access permissions for access to the laboratory instrument via the second user interface apparatus are only assigned if the at least one further predetermined condition is also satisfied. This further condition or these further conditions may be dependent on the use case. Similar conditions can, in general, be taken into account by the access control device when a decision is made about the allocation of authorizations and/or access permissions to a logging-on or logged-on user.

Possible use cases are, for example, in each case preferably, the observation of the laboratory instrument by means of a remote data connection ("remote monitoring"), the control of the laboratory instrument by means of a remote data connection ("remote control"), the use of a booking schedule for time-dependent planning of the use of the laboratory instrument by a plurality of users ("booking schedule"), the pre-programming of a treatment, in particular of a program-controlled treatment, in particular by process programming ("pre-programming") or the remote access by a service technician ("remote service access"). The condition can furthermore take into account the role of the user and/or the operating state of the laboratory instrument. The operating state of the laboratory instrument can, in particular, be an idle state, i.e. a state without, in particular, a running treatment, in which, however, the laboratory instrument can be ready, in particular, for the log on of a user and/or for carrying out a treatment. The operating state of the laboratory instrument can, in particular, be a state in which a treatment is or was programmed and/or the treatment was prepared and is just about to be carried out. The operating state of the laboratory instrument can, in particular, be a state in which a treatment was already started and is running, or a state in which a treatment was stopped or a state in which the booking schedule has a booking entry for the treatment by a user, wherein a distinction can be made as to whether or not this user is logged on. The operating state of the laboratory instrument can, in particular, be an energy saving state ("standby" mode) of the laboratory instrument. Further examples of possible or preferred embodiments of such authorizations as a function of the aforementioned conditions are found in "Appendix 1" of the description.

Preferably, the access control device, in particular the control apparatus of the access control device, is configured in such a way that, in particular if a further condition is satisfied, information about the operating state of the laboratory instrument, measured values or settings and programs of the laboratory instrument which can be influenced by the user are transmitted to the second user interface apparatus via the interface apparatus. In particular, this condition may be that a user has requested this information transfer at the access control device.

Preferably, in an eleventh preferred configuration of the access control device, which, in particular, may comprise the ninth or tenth configuration, the access control device or the control apparatus of the access control device is configured in such a way that, if a) or b) is satisfied, information about the operating state of the laboratory instrument, measured values or settings and programs of the laboratory instrument which can be influenced by users are transmitted to the second user interface apparatus via the interface apparatus. As a result of this information transfer, the laboratory instrument, in particular a treatment running thereon, can continue to be observed and/or controlled by means of the second user interface apparatus. In particular, the use state of the first interface apparatus can be partly or completely copied or cloned in the second user interface apparatus. The information transfer can, in particular, be a synchronization process. The first and second user interface can be synchronized, in particular in this manner.

The aforementioned configurations of the laboratory instrument according to the invention and/or of the access control device according to the invention may be combined with other features mentioned within the scope of the description of the present invention.

Preferably, the access control device, in particular the control apparatus of the access control device, is configured in such a way that the settings which can be influenced by the user contain at least one program parameter for the program-controlled treatment of a laboratory sample, which, in particular, is controlled by means of a process program.

Preferably, the control apparatus of the access control device and/or the control apparatus of the laboratory instrument comprises a storage apparatus in which user qualification data are stored, in which are assigned for each user of the laboratory instrument a qualification in the form of at least one qualification value or certificate. Preferably, the access control device, in particular the control apparatus of the access control device, is configured in such a way that the authorizations and/or access permissions are granted to a user, in particular, the latter is assigned a role, as a function of his qualifications. As a result of this, users may use the laboratory instrument in accordance with their qualification, as a result of which, in particular, inexperienced users are not overwhelmed. As a result, the productivity and operational safety during use of the laboratory instrument are increased.

Preferably, the control apparatus of the access control device and/or the control apparatus of the laboratory instrument are embodied to carry out a qualification method for at least one user, in which the at least one user runs through a qualification exam, which is carried out and evaluated by the control apparatus, and wherein the qualification method in particular provides for the data entered by the at least one user as a response to specific questions to be evaluated and in particular provides for the at least one user to be assigned a qualification, in particular in accordance with a comparison table or a computational prescription, as a function of the result of this evaluation. Such a qualification method carried out on the access control device or on the laboratory instrument is particularly practically relevant and therefore efficient.

Preferably, the control apparatus of the access control device and/or the control apparatus of the laboratory instrument are embodied, by means of the access control device, to grant and/or withdraw certain access permissions to functions of the laboratory machine to or from the user, depending on his qualification.

Preferably, the control apparatus of the access control device and/or the control apparatus of the laboratory instrument are embodied to display to the user, depending on his qualification, at least one graphical user interface, which corresponds to the qualification, on the display of the user interface apparatus and/or, in particular, to make available or not make available certain assistance programs and/or auxiliary information.

Preferably, the control apparatus of the access control device and/or the control apparatus of the laboratory instrument comprises a timer, in particular a clock, and/or, in particular, a booking apparatus, which comprises a storage apparatus which stores booking data, which, in particular, contain at least one booking data record or a plurality of booking data records, which describe at least one booking schedule, in particular individually for each treatment apparatus.

A booking data record contains, in particular, at least one of the items of information, in particular, which user, in particular at what time, carries out, has carried out or will carry out, in particular, which treatment of samples, in particular by means of which laboratory instrument. The booking data preferably contain information about the bookings accepted by the booking apparatus, which bookings were in fact confirmed after comparison with the free capacities present in the booking schedule and were recorded in the booking schedule. However, the booking data may also contain booking requests, which the booking apparatus can recheck, in particular even at a later time after the request was placed, and possibly accept at a later date, for example if an earlier entry in the reservation schedule was subsequently cancelled. The reservation data record preferably also contains information about what type of treatment is in each case planned on a laboratory instrument, what specific period of time or what duration of occupying the laboratory instrument is envisaged in the process and/or information about the process program used, and preferably contains, in particular, at least one program parameter or control parameter.

Preferably, the access control device is configured to transmit to a user upon request at least one item of information about the booking schedule, in particular to transmit the whole or part of the booking schedule or to transmit at least one change in the booking schedule. Preferably, the access control device is configured to transmit a notification automatically to a user, depending on at least one condition. This condition could be the change in the reservation schedule of a laboratory instrument, in particular in relation to the availability of a date for carrying out a treatment, in particular the release or cancelling of a date.

The "type of treatment" is, in particular, predetermined by the program parameters characterizing treatment. Such program parameters are, in particular, used by the control apparatus to generate a process program. In particular, a process program is a control code for controlling the treatment by means of control parameters. In particular, the control parameters are generated by the control apparatus, in particular by a control program running on the control apparatus, e.g. an operating system, while using the program parameters. The treatment of a sample is carried out, in particular, by virtue of a process program being executed by the control apparatus.

A "type of treatment" means a process, namely a type of application (e.g. "MagSep Blood gDNA", "Compose Mastermix" etc.). In a preferred configuration of the laboratory instrument as laboratory machine, the user initially selects a desired application, i.e. a "type of treatment", by virtue of selecting an application, in particular on the touchscreen of an instrument. This application, which is also referred to as "process", is, in particular, assigned to a program module which, in particular, may be a constituent of the control program. In particular, at least one program parameter is queried by the user by means of the program module. A program module generates, in particular, a process program on the basis of the at least one program parameter selected by the user.

Preferably, the control apparatus of the access control device and/or the control apparatus of the laboratory instrument is embodied to store booking data in the storage apparatus of the booking apparatus.

Preferably, the control apparatus of the access control device and/or the control apparatus of the laboratory instrument is configured to record the booking data record entered by a user into the laboratory instrument, in particular by means of the user interface apparatus or a portable or mobile user interface apparatus.

Preferably, the control apparatus of the access control device and/or the control apparatus of the laboratory instrument is embodied to compare the booking data record entered by the user with booking data already stored in the storage apparatus of the user interface apparatus.

Preferably, the control apparatus of the access control device and/or the control apparatus of the laboratory instrument is configured to store at least one, some or all booking data records, entered by at least one user, in the storage apparatus.

Preferably, the control apparatus of the access control device and/or the control apparatus of the laboratory instrument is embodied to evaluate some or all booking data records, entered by at least one user and stored in the storage apparatus, in accordance with an evaluation method stored in the storage apparatus and to create the schedule according to at least one criterion by virtue of the booking data records being sorted in accordance with the at least one criterion of a sort method stored in the control apparatus.

Preferably, the control apparatus of the access control device and/or the control apparatus of the laboratory instrument is embodied to assign the at least one booking data record a priority by means of an evaluation method, which priority is established in accordance with at least one criterion.

The criterion can, in particular, be represented by a data table stored in the control apparatus, in which data table e.g. the priority is related to at least one other parameter, wherein this other parameter may characterize e.g. the user or a user group, or the classification of a treatment in accordance to a list of relevance (e.g. from important to unimportant, expensive to cost-effective, etc.).

Preferably, the control apparatus of the access control device and/or the control apparatus of the laboratory instrument is embodied in such a way that the sort method sorts at least two booking data records in accordance with at least one criterion in order, in particular, to create a schedule which uses other time data than what is provided for in the booking data records of the users.

The criterion can be selected in accordance with the definitions in the evaluation method. Preferably, in order to realize a preferred criterion, the control apparatus is embodied to sort the booking data records under the aspect of a resource being optimized.

By way of example, the resource can be the time; in particular, a minimization of the waiting times can be sought after, a user in each case experiencing said waiting times as the difference between the start time, as desired by said user, and the start time, assigned by the laboratory instrument after evaluation and sort, for the experiment of said user, i.e. the treatment desired by said user. The minimization of the passive time, during which a laboratory instrument is not used, may also be sought after. In particular, it is also possible to plan intermediate servicing, cleaning and/or sterilization procedures, during which e.g. at least one workspace of at least one laboratory instrument or laboratory machine is prepared, in particular prepared manually and/or automatically, and/or cleaned and/or sterilized.

The resource may also be the energy which, as a function of the sequence of treatments, is possibly consumed to a different extent over different and successively carried out ones of said treatments.

The resource may be a consumable, in particular a substance, e.g. a cleaner, or specific transport containers, e.g. pipette tips, or storage containers, e.g. microtiter plates, which, as a function of the sequence of treatments, are consumed to a different extent over various and successively carried out ones of said treatments. The same processes are possibly used in treatments planned by different users, and so it may be efficient to sort bookings on the basis of the processes. By way of example, it is conceivable that a specific substance and/or a specific consumable and/or a specific tool is used in a plurality of processes planned by different (or the same) users. Then, it may be particularly efficient to store this substance or this consumable or this tool in the laboratory instrument such that some transport processes become superfluous, as a result of which time and, optionally, the resource itself are saved, which resources often need to be stored under sterile conditions. By way of example, it would also be possible for two treatments, provided temporally in succession in the booking schedule, to be able to share specific consumables. By way of example, one and the same storage container could be used in both treatments, and therefore it is efficient to use the storage container for the second treatment after completion of the first treatment instead of disposing of the first storage container at the end of the first treatment and using a further storage container at the beginning of the second treatment. Moreover, it would for example also be possible to combine two separate bookings for an identical treatment and to work together in a single consumable (microtiter plate) in one treatment. As a result, it is possible to save material and time in many situations.

The resource can also be the plurality of laboratory instruments, on which the bookings occurring during a booking period of time are to be distributed automatically in accordance with the plurality of booking data records from a plurality of users in order to obtain an optimal use of the parks of laboratory instruments available in a laboratory. In particular, there may be experiments which require the synchronized use of more than one laboratory instrument. The resource may therefore consist of using a plurality of laboratory instruments optimally in time, in particular taking into account at least one experiment or a plurality of experiments which may each require different laboratory instruments.

By way of example, it is possible that a higher ranked role, e.g. an "administrator", is able to delete or move previously booked booking entries in the booking schedule, for example because an (external) service technician wishes/needs to service the treatment apparatus(es) on said date or because of other aforementioned reasons. Particularly from the view of the customer, an action without consultation is not preferred, rather a note to the user(s) of the booked one or more treatment apparatuses to the effect that the use of the treatment apparatus needs to be moved to a later date is preferable. In this context, proposing a suitable alternative time may also be expedient. The control apparatus is preferably embodied to emit such a notification via the user interface apparatus of the relevant user, in particular by using a remote data connection.

To the extent that a treatment apparatus is in strong demand, a booking mechanism, which is designed as a FIFO list (FIFO—first in, first out) and which in turn is used for informing the top-most user the moment the treatment apparatus becomes unoccupied, is particularly suitable. This information then preferably also comprises the timeframe for which the treatment apparatus is available. The topmost user would then receive the priority to occupy the treatment apparatus for a defined period of time. If he does not do this, the user is removed from the list and the option for occupation is transferred to the next user on the list, etc.

The term "instrument-controlled treatment" means that the treatment of the at least one laboratory sample is at least partly controlled, in particular performed, by the laboratory instrument. To the extent that the treatment is controlled and/or carried out by the laboratory instrument, said treatment in this respect is, in particular, not controlled and/or performed by the user, in particular not controlled and/or performed manually by the user.

An instrument-controlled treatment is furthermore preferably understood to mean that the treatment is at least partly controlled, in particular performed, by the laboratory instrument as a function of at least one user input. The user input may occur prior to the start of the treatment and/or during the treatment. The user input preferably occurs using a user interface apparatus, which is preferably a component of the laboratory instrument or which is provided separately from the laboratory instrument and signal connected to the control apparatus of the laboratory instrument and/or to the control apparatus of the access control device. The user input serves, in particular, for entering at least one parameter, the value of which influences and/or controls the treatment. This paramter can, in particular, be a program parameter.

The "instrument-controlled treatment" denotes, in particular, the at least partly automated treatment. In the case of a partly automated treatment, it is possible, in particular, for the treatment to be performed in such a way that, after the treatment has started and before the treatment is complete, there is at least one user input, by means of which the user can influence the current treatment, in particular by virtue of said user e.g. responding to an automatic query brought about by means of a user interface apparatus of the laboratory instrument, in particular by virtue of confirming or denying an input or undertaking other inputs. In the case of the partly automated treatment, it is possible, in particular, for the treatment to have a plurality of treatment steps which, in particular, are performed automatically and successively in time and which have at least one treatment step that requires a user input, which, in particular, is brought about via a user interface apparatus.

An instrument-controlled treatment is preferably a program-controlled treatment, i.e. a treatment controlled by a program. A program-controlled treatment of a sample should be understood to mean that the process of treatment substantially takes place by working through a plurality or multiplicity of program steps. Preferably, the program-controlled treatment takes place using at least one program parameter, in particular at least one program parameter selected by the user. A parameter selected by a user is also referred to as a user parameter. The program-controlled treatment preferably takes place with the aid of a digital data processing apparatus which, in particular, may be a component of the control apparatus of the laboratory instrument. The data processing apparatus can comprise at least one processor, i.e. a CPU, and/or at least one microprocessor. The program-controlled treatment is preferably controlled and/or performed in accordance with the prescriptions of a program, in particular a control program. In particular, substantially no user activity is required in the case of a program-controlled treatment, at least after acquisition of the program parameters required from the user.

A program parameter is understood to mean a variable which can be set in a predetermined manner within a program or sub-program and is valid for at least one execution (call) of the program or sub-program. The program parameter is set, e.g. by the user, and controls the program or sub-program and causes a data output as a function of this program parameter. In particular, the program parameter influences and/or controls the control of the instrument, and/or the data output by the program control said instrument, in particular the control of the treatment by means of the at least one treatment apparatus.

A program parameter may be a program parameter required on the part of the user. A program parameter required on the part of the user is distinguished by the fact that it is required for performing a treatment, in particular for performing a process program. Other program parameters, which are not required on the part of the user, may be derived from the program parameters required on the part of the user or may be made available in a different manner, in particular they may optionally be set by the user. In particular, a program parameter is set by a user by displaying a selection of possible predetermined values from a list of predetermined values stored in the laboratory instrument, wherein the user selects, and therefore sets, the desired parameter from this list. It is also possible for this program parameter to be set by virtue of the user entering the value, e.g. by virtue of entering a number corresponding to the desired value by means of a numeric pad or by virtue of said user increasing or reducing a value continuously or in increments until said value corresponds to the desired value and the value is set thus. Other forms of entry, e.g. by voice control and/or gesture control, are conceivable.

A program is, in particular, understood to mean a computer program. A program is a sequence of statements, in particular consisting of declarations and instructions, enabling a specific functionality, object or problem to be handled and/or solved on a digital data processing system. A program is generally available as software which is used with a digital data processing system. In particular, the program can be available as firmware, in particular as firmware of the control apparatus of the laboratory instrument and/or of the access control device in the case of the present invention. The program is usually available as a program file, often in the form of so-called machine code, which can be executed on a data medium, which program file is loaded into the main memory of the computer of the digital data processing system for execution purposes. The program is processed and therefore executed by the processor(s) of the computer as a sequence of machine commands, i.e. processor commands. In particular, a "computer program" is also understood to mean the source text of the program from which the executable code can be generated in the progress of the control of the laboratory instrument.

As is conventional, a statement denotes a central element of a programming language. Programs of such languages are primarily composed of one or more statements. A statement constitutes a single prescription, formulated within the syntax of a programming language, which prescription is to be executed when working through the program. The syntax of a statement is set by the respective programming language or the specification thereof. In machine-oriented programming, statements are often also referred to as commands.

Statements are usually assignments, control statements (such as branches, loops and conditional statements) and procedural calls. Depending on the programming language, assertions, declarations, class definitions and function definitions are also in part statements. Thus, the statements of the control program can be configured in a conventional manner.

As is conventional, a program module is understood to be a complete functional unit of software, consisting of a sequence of processing steps and data structures. Here, in particular, the following definitions may apply: the content of a module is often a recurring calculation or handling of data, which needs to be carried out a number of times. Modules offer an encapsulation by separating interface and implementation: the interface of a module defines the data elements which, as input and result of the processing, are required by the module. The implementation contains the actual program code. By way of example, a module is called as a function or sub-program, executes a number of processing steps and, as a result, provides data back to the calling program. A module itself is able to call further modules—thus, a hierarchy of program calls is possible. The data structures and processes set in modules can, when necessary, be inherited and inherited by other modules. Therefore, modules are an essential element in structured and object-oriented programming.

A control program is understood to mean an executable computer program, which preferably controls and/or performs the desired treatment of the at least one sample, in particular as a function of at least one program parameter. This program parameter can be a program parameter influenced and/or set by the user. In particular, the treatment can be controlled by virtue of the control apparatus generating one or more control parameters as a function of the program parameters, by means of which control parameters the at least one treatment apparatus is controlled. The laboratory instrument preferably has an operating system, which can be or comprise a control program. In particular, the control program can denote an operating system of the laboratory instrument or a component of the operating system. The operating system controls the treatment and further operating functions of the laboratory instrument.

In particular, the control program can be signal connected to the access control device and/or can control the access control device. The control apparatus of the access control device can be integrated into the control apparatus of the laboratory instrument or can be embodied separately from this control apparatus. The access control device can be integrated into the control apparatus of the laboratory instrument. The control device of the access control device can be integrated into control device of the laboratory instrument, can be controllable by the control program and/or can, in particular, be integrated into the control program. The control program can control further preferably provided functions of the laboratory instrument, for example an energy-saving function of the laboratory instrument or a communication function for communication with external data processing apparatuses which, in particular, are provided separately from the laboratory instrument and, in particular, are not a component of the laboratory instrument.

A process program is understood to mean a program which determines the specific progress of a treatment, in particular in accordance with a predetermined type of treatment and/or in accordance with a manner set on the part of the user.

The invention furthermore relates to a laboratory instrument for instrument-controlled treatment of at least one laboratory sample, which laboratory instrument comprises at least one treatment apparatus for performing the treatment of the at least one laboratory sample, and an access control device according to the invention.

Preferably, the laboratory instrument comprises a communication apparatus for establishing a remote data connection for data interchange with an external instrument, which likewise comprises a suitable communication apparatus for establishing a remote connection for data interchange with the laboratory machine. Such a communication apparatus can be embodied for establishing a radio connection, in particular a mobile communications connection. The communication apparatus is preferably configured to enable remote access of a user to the laboratory instrument, in particular for selecting or setting of at least one parameter, in particular a parameter which controls a function of the laboratory instrument, in particular the function of performing a treatment.

Preferably, the control apparatus of the access control device or of the laboratory instrument is embodied to provide synchronization data. Preferably, the access control device, in particular the control apparatus of the access control device, is configured in such a way that, if at least one condition is satisfied, information about the operating state of the laboratory instrument, measured values or settings and programs of the laboratory instrument which can be influenced by the user are transmitted to the second user interface apparatus via the interface apparatus. As a result of this information transfer, the laboratory instrument, in particular as a result of a treatment running thereon, can continue to be observed and/or controlled by means of the second user interface apparatus. In particular, the use state of the first interface apparatus can be partly or completely copied or cloned in the second user interface apparatus. The information transfer can, in particular, be a synchronization process. The first and second user interface can be synchronized, in particular in this manner. The at least one condition may be that the access of the accessing user is brought about by means of a remote data connection via a (mobile) user interface apparatus and the request of the user occurs after synchronization. The at least one condition can moreover be condition a) or b), namely the response to the check whether the logging-on user has already previously, by means of a first user interface apparatus, a) activated one or more of the currently performed functions of the laboratory instrument or b) is already logged on. In cases a) and b), the synchronization would only be allowed for a user with an active session and/or with currently activated functions on the laboratory instrument, in particular with running treatments which were initiated by the user. However, it is also possible and preferred for a further user to be allowed to carry out synchronization, e.g. in order to perform remote control for the purpose of providing assistance during a current session or treatment or for the purpose of carrying out servicing works, etc.

Preferably, the control apparatus of the access control device is configured to transfer these synchronization data to an—in particular mobile—user interface apparatus. Preferably, these synchronization data are suitable for displaying the information displayed in the display of the user interface apparatus at least partly in an identical manner on the display of the—in particular mobile—user interface apparatus.

The term laboratory instrument denotes, in particular, an instrument which is embodied for instrument-controlled treatment of at least one laboratory sample and which is embodied for use in a laboratory. This laboratory can be, in particular, a chemical, biological, biochemical, medical or forensic laboratory. Such laboratories serve for research and/or analysing laboratory samples, but can also serve for the manufacture of products by means of laboratory samples or the manufacture of laboratory samples.

A laboratory instrument is preferably one of the following laboratory instruments and/or is preferably embodied as at least one of the following laboratory instruments: a laboratory centrifuge, also referred to as "centrifuge" within the scope of the description of the present invention; a thermocycler, also referred to as "cycler" within the scope of the description of the present invention; a laboratory spectral photometer, also referred to as "biospectrometer" within the scope of the description of the present invention; a cell counting instrument, also referred to as "cell counter" within the scope of the description of the present invention, in particular optical counting instruments; a laboratory incubator, also referred to as "incubator" within the scope of the description of the present invention; a laboratory shaker, also referred to as "shaker" within the scope of the description of the present invention; a laboratory mixer, also referred to as "mixing device"; a laboratory freezer, also referred to as "freezer" within the scope of the description of the present invention; a bioreactor, also referred to as fermenter within the scope of the description of the present invention; a safety work bench, in particular biological safety cabinet, also referred to as "biosafety cabinet" within the scope of the description of the present invention; a sample plate reader, also referred to as "plate reader" within the scope of the description of the present invention, in particular "microplate reader"; a laboratory machine for treating fluid samples, in particular a pipetting machine.

A laboratory centrifuge is an instrument which works using inertia. The laboratory centrifuge, in particular the treatment apparatus of the laboratory centrifuge, comprises, in particular, at least one rotor, in which the at least one laboratory sample can be disposed. The at least one rotor is disposed rotatably in at least one centrifuge vessel. The laboratory centrifuge, in particular the treatment apparatus of the laboratory centrifuge, comprises at least one drive apparatus, by means of which the rotation is driven and/or braked. The samples can be disposed in the at least one rotor, preferably in laboratory containers, e.g. sample tubules, which are disposed in suitable holders in the rotor. The laboratory centrifuge, in particular the treatment apparatus of the laboratory centrifuge, preferably comprises at least one heater/cooling apparatus, by means of which the temperature of the at least one sample disposed in the rotor can be controlled and/or regulated. The laboratory centrifuge, in particular the treatment apparatus of the laboratory centrifuge, preferably comprises a timer apparatus, by means of which time parameters of the rotation or temperature settings can be controlled. The functionality is based upon the centrifugal force, which occurs due to a uniform circular motion of the samples to be centrifuged. The centrifugal force is used for substance separation of substances with different densities, which are contained in a sample. A centrifuge can perform a separation method, in which, in particular, the constituents of suspensions, emulsions and/or gas mixtures are separated. The instrument-controlled treatment of the at least one laboratory sample corresponds to a rotational treatment in a laboratory centrifuge, with at least one sample being subjected to said rotational treatment. Possible parameters, in particular program parameters, in particular user parameters, which are used to influence a rotational treatment, define, in particular, a temperature of the laboratory centrifuge, a rotational speed of the laboratory centrifuge, a time parameter of the rotation or a temperature setting and/or at least one progress parameter, which influences or defines the progress, in particular the sequence, of a rotation program consisting of a plurality of rotation steps. The temperature of the laboratory centrifuge can, in particular, be at least one temperature in the interior of the at least one rotor, in particular at least one temperature of at least one sample.

A thermocycler is an instrument that is able, successively in time, to set the temperature of at least one sample to a predetermined temperature and to keep said sample at this temperature level for a predetermined duration. The progress of this temperature control is cyclical. That is to say, a predetermined temperature cycle, i.e. a sequence of at least two temperature levels, is carried out repeatedly. This method serves, in particular, for performing a polymerase chain reaction (PCR). In this context, a thermocycler is sometimes also referred to as a PCR block. A thermocycler, in particular the treatment apparatus of the thermocycler, preferably has a thermoblock. A thermoblock is a sample holder made of a heat-conducting material, usually a metal-containing material or a metal, in particular aluminium or silver. The sample holder comprises a contacting side which is contacted by at least one heater/cooling apparatus of the thermocycler, in particular by a Peltier element. The thermocycler, in particular the treatment apparatus of the thermocycler, comprises a regulation apparatus with at least one control loop, to which the at least one heater/cooling apparatus is assigned as an actuator and at least one temperature measurement apparatus is assigned as a measurement member. The temperature is regulated to a temperature level by means of the controlling system. A cooling body of the thermocycler, in particular of the treatment apparatus of the thermocycler, serves for cooling sections of the thermocycler, in particular for cooling the Peltier elements. The thermocycler, in particular the treatment apparatus of the thermocycler, may comprise further heater and/or cooling elements. The thermocycler, in particular the treatment apparatus of the thermocycler, preferably comprises a timer apparatus, by means of which time parameters for setting the temperature cycle can be controlled. The instrument-controlled treatment of the at least one laboratory sample corresponds to a temperature cycle treatment in a thermocycler, with at least one sample being subjected to said rotational treatment. Possible parameters, in particular program parameters, in particular user parameters, which are used to influence a temperature cycle treatment, define, in particular, the temperature of a temperature level, the duration of a temperature level, the control of further heater and/or cooling elements and/or the number of temperature levels or cycles and/or at least one progress parameter, which influences or defines the progress, in particular the sequence, of a temperature monitoring program consisting of a plurality of steps.

A laboratory spectrophotometer is an instrument which, by illuminating at least one measurement volume of at least one laboratory sample, usually over the whole spectrum of visible light from infrared to ultraviolet, establishes the values of diffuse reflection. Diffuse reflection refers to the situation in which a measurement volume absorbs part of the light spectrum and transmits part of the spectrum (transparent media) or reflects it (opaque media). The laboratory spectrophotometer is used, in particular, to measure the absorptivity of a sample as a function of the light wavelength. Moreover, it is possible, in particular, to extend the field of application of the laboratory spectrophotometer by means of various modules. By way of example, it is conceivable to dispose a fluorescence module for measuring fluorescence or a temperature-control module for controlling the temperature of the sample in the spectrometer. The measured absorption spectrum contains, in particular, the light intensities measured at specific wavelengths. The absorption spectrum is typical of the laboratory sample or the substance contained therein or the substances contained therein. This can be used for qualitative analysis of the laboratory sample. If the liquid sample or the substance dissolved therein is known, the concentration of the dissolved substance can be established by measuring the absorption. This can be used for quantitative analysis of the laboratory sample. The laboratory spectrophotometer, in particular the treatment apparatus of the laboratory spectrophotometer, preferably comprises at least one light source, preferably at least one timer, preferably at least one photodetector. The instrument-controlled treatment of the at least one laboratory sample corresponds to a light and measurement treatment in a laboratory spectrophotometer, with at least one sample being subjected to said treatment. Possible parameters, in particular program parameters, in particular user parameters, which are used to influence a light and measurement treatment, define, in particular, the optical light spectrum, by means of which the at least one sample is irradiated and/or at least one progress parameter, which influences or defines the progress, in particular the sequence, of a light and measurement treatment program consisting of a plurality of steps.

A cell counting instrument serves for counting biological cells or particles which are contained in a laboratory sample. There are different physical principles which can be used to count cells, in particular optical methods, in which the laboratory sample to be measured is disposed in a counting chamber and there is additional illumination, particularly in the case of automatically operating ones, and an image of the cells or particles disposed in the counting chamber is acquired and evaluated. A further established method lies in measuring the impedance: a cell counting instrument embodied as a Coulter counter guides the laboratory sample containing the cells through an aperture ("measurement port"). Each passage of a cell through the aperture is detected electrically as a countable event. Optical cell counting instruments, in particular the treatment apparatus of the cell counting instrument, preferably comprise, depending on the embodiment, at least one light source, at least one image acquisition unit and at least one image evaluation unit*, and additionally, inter alia, a positioning apparatus. The instrument-controlled treatment of the at least one laboratory sample corresponds e.g. to a light and measurement treatment in the case of an optical cell counting instrument, a pumping and measurement treatment in the case of an instrument operating according to the Coulter principle, to which treatment the at least one sample is subjected. Possible parameters, in particular program parameters, in particular user parameters, which are used to influence a light and measurement treatment or the pumping and measurement treatment, define, in particular, the light intensity of the light source, by means of which the at least one sample is irradiated and/or at least one progress parameter, which influences or defines the progress, in particular the sequence, of a light and measurement treatment program or the pumping and measurement treatment program consisting of a plurality of steps. Moreover, in the case of optical counting instruments, the algorithms necessary for the image evaluation, and the sequence and parameterization thereof are decisive for the significance of the measurement result. Optical measurement instruments, but also Coulter counters, often use counting chambers for single use ("consumables"); these are plastic articles in the style of conventional Neubauer counting chambers or, in the case of Coulter counters, "lab-on-a-chip"-like disposable counting chambers. However, there are also instruments which operate without these consumables (e.g. "CASY").

A laboratory incubator is an instrument by means of which controlled climatic conditions for various biological development and growth processes can be set up and maintained. It serves to set up and maintain a microclimate with regulated gas and/or humidity and/or temperature conditions in an incubator space, wherein this treatment may be dependent on time. The laboratory incubator, in particular the treatment apparatus of the laboratory incubator, may, in particular, comprise a timer, in particular a timer switch, a heater/cooling apparatus and preferably a setting for regulating a substitute gas supplied to the incubator space, in particular fresh air, a setting apparatus for the composition of the gas in the incubator space of the laboratory incubator, in particular for setting the $CO_2$ and/or $O_2$ content of the gas and/or a setting apparatus for setting the humidity in the incubator space of the laboratory incubator. The laboratory incubator, in particular the treatment apparatus of the laboratory incubator, comprises, in particular, the incubator space, furthermore preferably a regulation apparatus with at least one control loop, to which at least one heater/cooling apparatus is assigned as an actuator and at least one temperature measurement apparatus is assigned as a measurement member. The temperature can be regulated in the incubator by means of the controlling system. $CO_2$ incubators serve, in particular, for cultivating animal or human cells. Incubators may have turning devices for turning the at least one laboratory sample and/or a shaker apparatus for shaking or moving the at least one laboratory sample. The instrument-controlled treatment of the at least one laboratory sample corresponds to a climate treatment in a laboratory incubator, with at least one sample being subjected to said treatment. Possible parameters, in particular program parameters, in particular user parameters, which are used to influence a climate treatment, define, in particular, the temperature of the incubator space, in which the at least one sample is incubated, the $O_2$ and/or $CO_2$ partial pressure in the incubator interior, the humidity in the incubator interior and/or at least one progress parameter, which influences or defines the progress, in particular the sequence, of a incubation treatment program consisting of a plurality of steps.

A laboratory shaker serves for moving a laboratory sample, in particular for mixing a laboratory sample comprising a plurality of constituents. There are different embodiments of laboratory shakers, in particular overhead shakers or flatbed shakers. Laboratory shakers can comprise a temperature control function for controlling the temperature of at least one laboratory sample and can, in particular, comprise an incubator function for incubating the at least one laboratory sample in controlled climatic conditions. Laboratory shakers, in particular the treatment apparatus thereof, can, in particular, be configured to perform an oscillating motion. Laboratory shakers, in particular the treatment apparatus thereof, comprise, in particular, a drive for driving the motion, comprise, in particular, a timer apparatus, by means of which time parameters of the setting of the shaker treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a shaker treatment in a laboratory shaker, with at least one sample being subjected to said treatment. Possible parameters, in particular program parameters, in particular user parameters, which are used to influence a shaker treatment, define, in particular, the movement intensity, in particular the movement frequency in the case of an oscillating drive, of a time period during the shaker treatment and/or at least one progress parameter, which influences or defines the progress, in particular the sequence, of a shaker treatment program consisting of a plurality of steps.

A laboratory mixer, also referred to as "mixing device", serves like the laboratory shaker for moving a laboratory sample, in particular for mixing a laboratory sample comprising a plurality of constituents. Compared to a laboratory shaker, a laboratory mixer enables movements with higher frequencies, in particular with higher rotational speeds. Laboratory mixers, in particular the treatment apparatus thereof, can, in particular, be configured to perform an oscillating motion. Laboratory mixers, in particular the treatment apparatus thereof, comprise, in particular, a drive for driving the motion, comprise, in particular, a timer apparatus, by means of which time parameters of the setting of the mixer treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a mixer treatment in a laboratory mixer, with at least one sample being subjected to said treatment. Possible parameters, in particular program parameters, in particular user parameters, which are used to influence a mixer treatment, define, in particular, the movement intensity, in particular the movement frequency in the case of an oscillating drive, of a time period during the mixer treatment and/or at least one progress parameter, which influences or defines the progress, in particular the sequence, of a mixer treatment program consisting of a plurality of steps.

A laboratory freezer serves for storing at least one laboratory sample in a freezer room at regulated temperatures, in particular in the freezer range from −18° C. to −50° C. or in the ultra-freezer range from −50° C. to −90° C. In particular, a laboratory freezer is not a refrigerator, which can be used for cooling at temperatures in the range from 0° C. to 10° C. or from −10° to 10° C. in particular. A laboratory freezer, in particular the treatment apparatus of the laboratory freezer, comprises, in particular, at least one cooling apparatus and at least one regulation apparatus with at least one control loop, to which the at least one cooling apparatus is assigned as an actuator and at least one temperature measurement apparatus is assigned as a measurement member. A laboratory freezer, in particular the treatment apparatus of the laboratory freezer, comprises, in particular, a monitoring measurement instrument for measuring the temperature and/or in particular at least one alarm apparatus, by means of which an alarm signal is emitted if the temperature measured in the freezer space departs from a permitted temperature range. A laboratory freezer, in particular the treatment apparatus of the laboratory freezer, can, in particular, comprise an information reader for reading information. This information can be contained in an information medium which can be connected to an article. This article can, in particular, be a sample container which can contain at least one laboratory sample. The information medium can, in particular, comprise an RFID chip or other identification features, such as e.g. a barcode, a data matrix code, a QR code, which can be read by suitable methods. The instrument-controlled treatment of the at least one laboratory sample corresponds to a low-temperature treatment in a laboratory freezer, with at least one sample being subjected to said treatment. Possible parameters, in particular program parameters, in particular user parameters, which are used to influence a low-temperature treatment, define, in particular, the temperature of the freezer space, in which the at least one sample is frozen and/or the information read process, which is preferably carried out when an article provided with an information medium is transferred from a user into the laboratory freezer.

A bioreactor comprises a container, in which specific microorganisms, cells, *algae* or plants (e.g. mosses) are cultivated (also: fermented) under conditions which are as ideal as possible. The operation of a bioreactor therefore is an application of biotechnology, which, in technical apparatuses, uses biological processes, in particular bioconversion or biocatalysis, or makes these available. Factors which can be controlled or monitored in most bioreactors, in particular by setting appropriate parameters, are the composition of the nutrient solution, the oxygen supply, temperature, pH, sterility and/or other factors. The purpose of cultivation in a bioreactor may be the harvesting of cells or constituents of cells, or the harvesting of metabolic products. By way of example, these can be used as an active ingredient in the pharmaceutical industry or as a basic chemical in the chemical industry. The breakdown of chemical compounds may also take place in bioreactors, such as e.g. in sewage water treatment in sewage works. The production of beer, wine and other such products likewise occurs in bioreactors. The most diverse type of organisms are cultivated in bioreactors for various purposes. A bioreactor can therefore have different configurations. It can be configured as stirred tank reactor, which can have a volume from a few milliliters to hundreds of liters and can be filled with nutrient solution. It can also be used or embodied as a fixed bed reactor or photobioreactor. A bioreactor can be part of a bioreactor system, preferably of a parallel bioreactor system. In such a parallel bioreactor system, a multiplicity of bioreactors are operated in parallel and controlled with high precision. A bioreactor, in particular the treatment apparatus thereof, comprises, in particular, a stirring apparatus for stirring the sample contained in the reactor container, in particular for stirring the nutrient solution. A bioreactor, in particular the treatment apparatus thereof, comprises, in particular, a pump apparatus for pumping the laboratory sample, which is preferably configured as nutrient solution. A bioreactor, in particular the treatment apparatus thereof, comprises, in particular, a setting apparatus for setting a gas content in the reactor container, in particular the content of $CO_2$ and/or $O_2$ or of dissolved oxygen (DO). A bioreactor, in particular the treatment apparatus thereof, comprises, in particular, a setting apparatus for setting, in particular regulating, a pH in the sample in the reactor container. The instrument-controlled treatment of the at least one laboratory sample corresponds to, in particular, a nutrient solution treatment in a bioreactor, with at least one sample, preferably embodied as nutrient solution, being subjected to said treatment. Possible parameters, in particular program parameters, in particular user parameters, which are used to influence a nutrient solution treatment, define, in particular, the temperature of the nutrient solution in the reactor container and/or the speed of the stirrer apparatus, in particular the rotational speed and/or the pump speed or the metering speed and/or a gas content in the nutrient solution, in particular $CO_2$ and/or $O_2$ or dissolved oxygen (DO) and/or the pH of the nutrient solution and/or at least one progress parameter, which influences or defines the progress, in particular the sequence, of a nutrient solution treatment program consisting of a plurality of steps.

A biological safety cabinet serves, in particular, for secure storage or stockpiling of hazardous materials, in particular for meeting a biological protection level. In particular, these levels are standardized in EU Directive 2000/54/EG on the protection of workers from risks related to exposure to biological agents at work and, in Germany, in the German Ordinance on Biological Substances. A biological safety cabinet is intended to prevent laboratory samples stored in a biological safety cabinet from endangering the surroundings if danger develops. In particular, safety is ensured by virtue of the atmosphere contained in the receiving region of the biological safety cabinet being replaced and, in particular, filtered. Here, in particular, this atmosphere is conveyed through the receiving region by a conveying apparatus and moved through a filter, which filters the atmosphere and, in particular, removes hazardous materials. The biological safety cabinet, in particular the treatment apparatus thereof, comprises, in particular, a conveying apparatus for conveying atmospheric gas, comprises, in particular, a timer apparatus for measuring a filter operation duration and a ventilator operation duration and/or comprises, in particular, a measurement apparatus for measuring a conveyed amount of atmospheric gas. The instrument-controlled treatment of the at least one laboratory sample corresponds, in particular, to an atmospheric gas treatment for treating the atmospheric gas, in which the at least one sample is stored, in a biological safety cabinet. Possible parameters, in particular program parameters, in particular user parameters, which are used to influence an atmospheric gas treatment, define, in particular, the temperature of the atmospheric gas in the receiving region and/or the flow speed of the atmospheric gas conveyed by the conveying apparatus, the amount of air conveyed, the filter operation duration and/or the ventilator operation duration.

A sample plate reader, also referred to as "plate reader" or "microplate reader", is a laboratory instrument for detecting biological, chemical or physical events of samples in microtiter plates. They are used in many different respects in research: for active ingredient research, bioassay validation, quality control and manufacturing processes in the pharmaceutical and biotech industry and in academic organizations. The sample plate reader can, in particular, comprise at least one light source or radiation source, can comprise at least one photodetector, can comprise a temperature control apparatus for the temperature control of the samples or the sample plates and can comprise a timer. Sample reactions can be tested in 6-1536 well microtiter plates. The most common format for sample plates, in particular microtiter plates, which are used in academic research laboratories or in clinical-diagnostic laboratories, is a 96 well plate (an 8 by 12 matrix) with a typical individual volume of between 100 and 200 µl per well. microtiter plates with a higher density (384 or 1536 well microtiter plates) are typically used in screening applications if the throughput (number of samples to be processed per day) and assay costs per sample become critical parameters, and these have a typical assay volume of between 5 and 50 µl per well. The treatment is, in particular, an optical measurement of the microtiter plate, in particular the measurement of an absorption, fluorescence intensity, luminescence, time-resolved fluorescence and/or fluorescence polarization. Possible parameters, in particular program parameters, in particular user parameters, which are used to influence a measurement, define, for example, the intensity of the light source, the sensitivity of the photodetector, a time duration and/or a temperature.

A laboratory machine for treating fluid samples, in particular an automatic pipette, serves for the program-controlled treatment of these samples. A laboratory machine can be a laboratory instrument or comprise at least one laboratory instrument of the aforementioned type and/or can be embodied to carry out at least one, some or all of the treatments that can be executed by this aforementioned laboratory instrument. A laboratory machine comprises the treatment apparatus for automatic, program-controlled treatment of the at least one laboratory sample, wherein the treatment is controlled by using a plurality of program parameters, which are at least partly selected by the user. In the process, the sample can, for example, be moved and/or transported by the laboratory machine or a treatment apparatus of the laboratory machine. The movement can be brought about by transport in movable sample containers or by guidance through tube systems, capillaries or pipette tips. Here, liquid samples are, in particular, transported by suction, i.e. by pipetting, or, more generally, by the application of pressure differences. By way of example, a sample can be divided or diluted by a treatment of the sample. The contents of a sample can be analysed or it is possible, e.g. by way of a chemical reaction, for new contents to be produced, in particular by using the sample. In the context of, in particular, handling and analysing DNA or RNA or the constituents thereof, laboratory machines aid in obtaining a wealth of information within a suitable period of time or in analysing many such samples. This treatment apparatus of a laboratory machine usually comprises a worktop with workstations, on which samples can be handled or stored in various ways. For the purposes of transporting e.g. liquid samples between various positions, in particular sample containers, the treatment apparatus usually comprises an instrument-controlled movement device and an instrument-controlled fluid-transfer apparatus, which can e.g. comprise a pipetting system. Both the transport of the samples and the treatment thereof at the various stations can be carried out in an instrument-controlled manner, in particular in a program-controlled manner. Then the treatment is preferably at least partly or completely automated.

The user of the laboratory machine can preferably set the type of treatment for the sample. Such a treatment type may, in particular, serve for:

nucleic acid purification, in particular:
"MagSep Blood gDNA": purification of genomic DNA from whole blood, in particular using the Eppendorf® MagSep Blood gDNA kit;
"MagSep Tissue gDNA": purification of genomic DNA from living tissue, in particular using the Eppendorf® MagSep Tissue gDNA kit;
"MagSep Viral DANN/RNA": purification of viral RNA or DNA from cell-free bodily fluids, in particular using the Eppendorf® MagSep Viral DNA/RNA kit;
and PCR applications, in particular:
"Compose Mastermix";
"Normalize Concentrations";
"Create Dilution Series";
"Setup Reactions".

A laboratory instrument, in particular the laboratory machine, is preferably embodied in such a way that the treatment of the at least one laboratory sample can be controlled automatically using the acquired program parameters. A laboratory instrument, in particular the laboratory machine, in particular the control program thereof, is preferably embodied in such a way that the entries undertaken by the user, in particular the at least one value of at least one program parameter, can be used, where necessary, to automatically establish further, required program parameters, in particular by calculation or comparison with data in a database of the laboratory machine. In particular, the control parameters preferably used for performing the treatment in detail are preferably determined automatically. As a result of these measures, the operation of the laboratory instrument becomes more convenient, the user is spared from, in particular, designing a program code since these steps are carried out, in particular automatically, by the laboratory instrument. In a preferred embodiment of the invention, all that is required from the user are the entries which are directly related to the treatment of the samples to be performed. Often, these are the same specifications that would also be necessary for performing the treatment manually and these are known to the user. By contrast, the parameters which relate to the control of the laboratory instrument, in particular the control parameters, need not be set in detail since these are preferably set automatically. Control parameters are the parameters required in detail for controlling the technical constituents of the treatment apparatus. Control parameters can be program parameters or can be parameters derived therefrom for the technical implementation, in particular automatically determined parameters.

Preferably, a laboratory instrument, in particular the laboratory machine, automatically selects the fitting set of program parameters following the treatment type selection by the user, wherein the program parameters thereof required on the part of the user are then queried from the user in steps (b) and (c). The set of program parameters can contain, firstly, the program parameters required on the part of the user and can contain, secondly, further program parameters. These further program parameters can be set automatically depending on the selected treatment type or can be set automatically depending on at least one or all program parameters entered by the user and/or can be stored in the storage apparatus. The stored parameter sets are preferably optimized for the type of treatment—or become optimized by the laboratory machine—such that the user preferably requires no specialist knowledge for optimizing the parameters. The control parameters which are necessary for performing the specific treatment by means of the treatment apparatus are derived from the program parameter set.

A program parameter set of program parameters specific to a treatment type is preferably defined for this treatment type. The program parameters of this program parameter set can, in particular, define the accessories to be used for the treatment, e.g. sample container, transport container and/or the further consumables and/or tools to be used.

The mapping between program parameter set and treatment type is stored in the storage apparatus of the laboratory instrument, in particular of the laboratory machine. Preferably, the laboratory machine is embodied in such a way that the user can store and/or use more such mappings in the laboratory instrument. The operation of the laboratory machines becomes particularly efficient by this mapping in combination with the clear and well-structured querying of the program parameters. This mapping is preferably brought about by using one or more program modules, wherein a program module is respectively tailored to a specific application:

Preferably, the laboratory machine comprises at least one program module, with a predetermined program module serving for controlling a predetermined laboratory problem for treating laboratory samples.

The at least one program parameter, in particular the program parameter required on the part of the user, is preferably selected from the following set of physical variables relevant to treating a laboratory sample by means of the treatment apparatus: sample number, dilution factor, target volume, position of the samples in a sample vessel holder or in a microtiter plate, sample temperature, times and/or time differences, temperatures or temperature differences, rates of change of such parameters, etc.

Preferably, the control program further contains statements so as to execute the following step; in particular, the control apparatus of the laboratory instrument is configured for carrying out the following step:

Generating a process program using the program parameters entered by the user and storing the process program in the storage apparatus, wherein the process program can be edited by the user. As a result, the use of the laboratory instrument, in particular of the laboratory machine, becomes even more flexible.

The laboratory machine can be modified in such a way that it can be used to perform further treatment types. This can be brought about by virtue of the files and/or programs or program constituents required for this, in particular a program module mapped to the treatment type, being subsequently transmitted to the laboratory machine, in particular the storage apparatus thereof.

A laboratory sample is a sample which can be treated in a laboratory. Instead of the term laboratory sample, the term "sample" is also used in the description of the invention. The sample can be a fluid. The sample can be liquid, gel-like, powdery or a solid-state body or comprise such phases. The sample can be a mixture of such phases, in particular a liquid mixture, a solution, a suspension, e.g. a cell suspension, an emulsion or dispersion. A solution is a homogeneous mixture of at least two substances. A liquid sample can be of a type which is usually handled in a biological, chemical or medical laboratory. A liquid sample can be an analysis sample, a reagent, a medium, a buffer etc. A solution has one or more dissolved solid, liquid or gaseous substances (solutes) and furthermore comprises a preferably liquid solvent which, in particular, forms the greater portion or greatest portion of the volume which forms the solution. The solvent may itself be a solution.

The treatment of a laboratory sample or samples can contain one or more of the processes specified below, in particular simultaneously or in succession:

transport of the laboratory sample, in particular by a transport apparatus, under the action of gravity and/or a force caused by the laboratory machine;

a contactless (non-invasive) physical treatment of the sample, in particular a thermal treatment, in particular heating and/or cooling, in particular controlling the temperature of the sample; or freezing or defrosting of the sample or a different thermal induction of a phase change of the sample, e.g. evaporation, condensation, etc.; a magnetic treatment of the sample; an optical treatment of the sample, in particular irradiating the sample with radiation, in particular light, in particular visible light, infrared light or UV light or detection of such radiation, in particular fluorescence light, from this sample; a magnetic treatment of a sample with magnetic constituents, in particular magnetic separation of magnetic constituents, in particular "magnetic beads", from a liquid phase of the sample; moving the sample, i.e. performing a mechanical treatment of the sample, in particular shaking, rotating, oscillating, vibrating, centrifuging, an acoustic treatment, in particular with ultrasound, in each case e.g. for the purpose of mixing the sample or of separating constituents within the sample or of transporting the magnetic constituents out of the sample or into the sample;

invasive physical treatment of the sample, i.e. performing a mechanical treatment of the sample: introducing stirring tools, e.g. stirring bar or magnetic stirrer bar, into the sample and stirring, introducing a sonotrode for acoustic or ultrasonic treatment, introducing transport means, in particular transport containers, into the sample, e.g. dispenser tip or pipette tip or hollow needle or tube; adding other auxiliary means into the sample;

chemical, biochemical or biomedical treatment of the sample: adding chemical (e.g. reactant, reagent, solvent, solute), biochemical (e.g. biochemical macromolecules, e.g. DNA, DNA constituents; pharmaceutical active ingredients) or biomedical (blood, serum, cell medium) substances;

storing the sample, in particular for a period of time defined in a program-controlled manner, in particular under specific physical conditions, e.g. at a specific temperature, temperatures or temperature changes, in particular repeated temperature changes, e.g. cyclically and/or periodically repeated temperature changes and/or setting a surrounding pressure, e.g. applying positive pressure or negative pressure, in particular a vacuum, and/or setting a defined surrounding atmosphere, e.g. a protective gas or a specific humidity, under specific radiation conditions, e.g. shielded against visible light, in the dark or under defined irradiation;

measuring or analysing the sample, in particular analysing by means of a non-invasive and/or invasive treatment of the sample, in particular in order to measure at least one or more chemical, physical, biochemical and/or medical properties of the sample, in particular counting of cells by means of a cell counter;

handling of the sample, in particular changing at least one property of the sample, in particular by means of non-invasive and/or invasive treatment of the sample.

This treatment is, in particular, under program control, using at least one program parameter.

In particular, this treatment is brought about in accordance with at least one control parameter which determines the treatment of the laboratory sample by means of the treatment apparatus. A control parameter can set a period of time, a moment in time, a specific sample volume and/or metering volume, a specific sample temperature, etc. A control parameter can relate to the automatic use of a specific transport head, a specific type of transport container, a specific type of sample container, one or more individual samples or of specific positions of these components in the workspace. A control parameter can relate to the treatment of an individual sample or the treatment of a plurality or multiplicity of samples.

A control parameter is preferably selected automatically by the laboratory instrument, in particular the laboratory machine, as a function of at least one program parameter; in particular, it is selected automatically as a function of the program parameters selected by the user. As a result, an advantage for the user is that he does not need to determine all control parameters individually. The user needs no knowledge about the programming of the laboratory instrument. Rather, the control parameters required for the treatment are selected by means of the program parameters entered by the user. As a result, the use of the laboratory instrument is particularly convenient.

A control parameter can also correspond to a program parameter.

The transport of a sample can be transport from a sample container into a transport container and/or from the transport container into a sample container or any other target location. This transport is, in particular, under program control, using at least one program parameter.

The transport container can be e.g. a dispenser container which comprises a movable plunger and an inlet/outlet opening. The plunger generates negative pressure or positive pressure in the dispenser container and thus sucks the sample into the container or reemits it. This process follows the displacement principle, i.e. the sample to be moved, which is usually liquid and therefore incompressible, is subjected to forced movement by virtue of the volume previously taken up by the sample being moved by the plunger. In general, this plunger is moved, in particular moved under program control, by a movement apparatus which is assigned to the laboratory machine.

The transport container can furthermore be a pipette tip. A pipette tip has an inlet/outlet opening and a second opening. The second opening is coupled to a suction apparatus such that a liquid sample can be sucked (pipetted) from a sample container into the transport container by means of negative pressure. The sample is emitted by ventilating the suction region, by means of gravity and/or positive pressure which e.g. is generated in the pipette tip by means of the second opening.

The transport container preferably consists partly or wholly of plastic. It is preferably a consumable article, which is typically only used for one treatment or a small number of treatment steps of the sample. However, the transport container can also consist partly or wholly of a different material.

The transport of a sample can be a transport of the sample from an initial position to a target position. The initial position may be present if the sample is disposed in a first sample container and the target position of this sample can be the position thereof in a second sample container, into which the sample is transferred. This type of transport is also referred to presently as sample transfer or transfer. In practice, a sample transfer is usually carried out in order to transfer a sample from a storage container, in which, for example, the sample was stored and/or which may, for example, contain a relatively large amount of the sample, into a second sample container, in which the sample is subjected to further treatment. This transport is, in particular, under program control, using at least one program parameter.

The transport container preferably is or can be connected to a transport apparatus of the laboratory machine.

A sample container can be an individual container, in which only a single sample is contained, or it can be a multiple container, in which a plurality of individual containers connected to one another are disposed.

A single container can be an open container or a sealable container. In the case of a sealable container, provision can be made for a covering element, in particular a sealing cap. The covering element can be securely connected to the container, e.g. as a hinged cover or hinged closure cap, or can be used as separate component.

In a multiple container, the plurality of single containers are preferably disposed in a fixed position with respect to one another, in particular in accordance with the crossing points of a grid pattern. This simplifies the automated approach to the positions and, in particular, the individual addressing of samples. A multiple container can be embodied as plate element, in which the individual containers are connected in such a way that they form a plate-shaped arrangement. The individual containers can be embodied as depressions in a plate or can be interconnected by web elements. The plate element can have a frame element, in which the single containers are held. These connections between components can be integral connections, i.e. cohesive connections and/or connections generated by a common injection moulding process, or they can be generated in a force-fit and/or form-fit manner. In particular, the plate element can be a microtiter plate.

Multiple containers can comprise a plurality (2 to 10) of single containers. They can furthermore comprise a multiplicity (more than 10) thereof, typically 12, 16, 24, 32, 48, 64, 96, 384, 1536 single containers. In particular, the multiple container can be a microtiter plate. A microtiter plate can be embodied in accordance with one or more industrial standards, in particular the industrial standards ANSI/SBS 1-2004, ANSI/SBS 2-2004, ANSI/SBS 3-2004, ANSI/SBS 4-2004.

The maximum sample volume that can be held by a transport container or sample container typically lies between 0.01 ml and 100 ml, in particular 10-100 μl, 100-500 μl, 0.5-5 ml, 5-25 ml, 25-50 ml, 50-100 ml, depending on the type of selected transport container or sample vessel.

A sample container can comprise an information region, which can contain information about the sample container or the content thereof. The information region can contain encoded information, e.g. a barcode or QR code or an RFID chip or information encoded differently. The information can have information for identifying the sample and/or a sample container. The laboratory machine can have an information reader for reading this information and preferably providing this to the control apparatus.

The sample container preferably consists partly or wholly of plastic. It is preferably a consumable article, which is typically only used for one treatment or a small number of treatment steps of the sample. However, the sample container can also consist partly or wholly of a different material.

The sample container preferably can be transported by a transport apparatus of the laboratory machine.

The laboratory instrument, in particular the laboratory machine, is preferably embodied to treat a multiplicity of samples in succession and/or in parallel. In particular, a laboratory instrument, in particular the laboratory machine, is preferably embodied to treat, in particular to transport, to empty and/or to fill, a multiplicity of sample vessels, in particular single containers and/or multiple containers, in a program-controlled manner.

Preferably, a laboratory instrument, in particular the laboratory machine, comprises exactly one workspace. Such a laboratory instrument, in particular the laboratory machine, is compact and can be suitable, in particular, for use on a laboratory table, wherein, in that case, it is also referred to as, in particular, a table-top instrument. By way of example, the table can be the workbench of a chemical, biochemical or biomedical laboratory. The laboratory instrument, in particular the laboratory machine, can also be embodied for set up in such a laboratory. A laboratory instrument, in particular a laboratory machine, with a workspace can furthermore be embodied as an independently operating instrument in such a laboratory or it can be included in an instrument assemblage.

The laboratory instrument, in particular laboratory machine, can also be embodied as a laboratory line, in which a plurality of workspaces are disposed next to one another in such a way that, by means of a transport device, a single, a plurality or a multiplicity of samples can be transported successively and/or in parallel between the workspaces. A workspace of a laboratory line is preferably embodied in such a way that a specific laboratory object, usually relating to the parallel and/or sequential treatment of a multiplicity of samples, is carried out. A high work throughput of the laboratory line is obtained as a result of this specialization of each workspace. In order to perform such a specific object, provision can be made for only one type of treatment of at least one sample or for only a few types of treatment, e.g. two to ten treatment types, to be performed in each workspace. A treatment apparatus for performing a treatment, which is characteristic for a specific laboratory instrument, as described within the scope of the description of the invention, can be disposed at each workstation. The transport device can comprise a guide-rail system and/or a robotic apparatus for program-controlled movement of samples or sample containers.

A laboratory instrument, in particular a laboratory machine, can be connected or connectable to an LIMS. LIMS is an abbreviation for laboratory information and management system. As usual, an LIMS is a software system which relates to data processing in an automated or partly automated chemical, physical, biological or medical laboratory. Such data can originate from measurements of the samples and/or relate to the control of the data handling. An LIMS preferably serves for measurement value acquisition and measurement value evaluation. LIMS is used to increase the work throughput in a laboratory and/or to optimize the efficiency of the treatment of laboratory samples.

A tool element can be e.g. a transport head for the fluid transfer, in particular a pipetting head, which can comprise a connection section for connecting one pipette tip (single channel pipetting head) or for connecting a plurality of pipette tips (multiple channel pipetting head). Liquid can be sucked into the at least one pipette tip if the latter is connected to the connection section by means of at least one pressure and gas-tight channel connected to the pipetting head. In the laboratory machine, this pipetting is performed, in particular, in a program-controlled manner; in particular, it is influenced by at least one program parameter. The transport head can also be a dispensing head which has at least one movement apparatus for moving a plunger of the dispenser tip. In the laboratory machine, the movement apparatus is moved, in particular, in a program-controlled manner; in particular, it is influenced by at least one program parameter. The transport head can serve for metering liquid, in particular for metering in different regions; a transport head can be embodied for metering a liquid sample with a volume that can be selected from a volume range specific to this transport head: e.g. 1-50 μL or 20-300 μL or 50-1000 μL, ("l" and "L" are each an abbreviation for liter). A transport head can be embodied as a single-channel head, in which only one sample is transported, or it can be embodied as a multi-channel head, in particular an eight-channel head or a 12-channel head, in which a plurality of samples are handled or transported in parallel. Preferably, provision is made for specific transport containers, which can be used depending on the respective type of transport head, in particular in accordance with the corresponding volume range.

A tool element can be e.g. a transport head for transporting objects, for example a carrier and/or gripper tool for carrying and/or gripping an object. A carrying tool can comprise a fastening section for detachably fastening the object to the carrying tool, e.g. by a force-fit and/or cohesive and/or magnetic connection between the object and the carrying tool. In this manner, it is possible within the work top or between a plurality of workspaces and/or work tops.

A tool element can furthermore be a treatment unit, e.g. for performing a thermal, acoustic, optical and/or mechanical treatment of at least one sample.

The laboratory machine can comprise an information reader in order to read information regarding a sample and/or a sample container and/or a treatment instruction for this sample and/or this sample container and, preferably, make this available to the control apparatus of the laboratory machine.

The laboratory machine preferably comprises at least one timer apparatus and/or preferably at least one timing apparatus in order to enable the time-dependent treatment of the samples. The time-dependent treatment is preferably controlled by a program, and, in particular, controlled by at least one program parameter.

In a preferred configuration of the laboratory machine according to the invention, the former is configured, as a function of the treatment type selected by the user and the program parameters entered by the user, to select automatically one or more of the following components for use in the program-controlled treatment:
- at least one suitable sample container, in particular suitable for holding a plurality of samples which are to be handled together, e.g. which are intended to be mixed or between which a chemical reaction or biochemical, biological or biomedical interaction is intended to occur;
- at least one suitable transport container, in particular a pipette tip and/or a dispenser tip;
- at least one suitable transport head, to which the preferably automatically selected transport container can be connected,
- at least one suitable tool element, which serves for performing the desired treatment.

Preferably, the laboratory machine according to the invention is configured, as a function of the treatment type selected by the user and the program parameters entered by the user, to select automatically one or more of the following control parameters for use in the program-controlled treatment:
- at least one period of time, during which a specific work step of the treatment is performed;
- at least one sample volume and/or metering volume;
- at least one work position of the at least one work top;
- movement parameters for setting the motion sequence of the robotic apparatus of the laboratory machine required for the desired treatment of the sample.

As a result of the automatic selection of the aforementioned components and/or the control parameters as a function of at least one program parameter, in particular as a function of the at least one program parameter selected by the user, an advantage resulting for the user is that he does not need to individually determine the selection of the components and control parameters himself. Rather, the control parameters required for the treatment are selected by means of the program parameters entered by the user. The user needs no knowledge about the programming of the machine. As a result, the use of the laboratory machine is particularly convenient.

By way of example, what it is possible to achieve by the automatic selection of the aforementioned components and/or the control parameters as a function of at least one program parameter is that the correct pipetting head is selected automatically on the basis of the user specifications (e.g. dilute 20 samples) or, in more general terms, that the correct tool, e.g. transport head and/or tool head, is used. That is to say, the user then does not need to decide what the ideal tool is, but only needs to decide what the desired treatment is, e.g. nucleic acid purification in a desired manner. The user, e.g. a biologist, a biological assistant or a medical assistant, then merely needs to make those decisions which he can make easily and quickly due to his training, but does not need to be fluent in an abstract programming language or make relatively complicated calculations.

The treatment apparatus of the laboratory machine comprises: preferably at least one workspace, preferably at least one transport apparatus and preferably at least one treatment unit.

Preferably, the laboratory instrument, in particular the laboratory machine, has the property of permanently storing the program parameters entered by the user and to load these again automatically—or following a user trigger at a later point in time. The user can then modify individual ones of the parameters in order to completely define a sample treatment type. As a result, the operating convenience is increased and the susceptibility to faults is decreased. This is advantageous against the backdrop that laboratory instruments are used particularly efficiently for repeating processes.

The laboratory instrument according to the invention preferably comprises a communication apparatus for establishing a remote data connection for data interchange with an external instrument, which likewise comprises a suitable communication apparatus for establishing a remote connection for data interchange with the laboratory machine.

The laboratory instrument preferably comprises a user interface apparatus for the manual entry of data by a user and for displaying information, in particular information contained in this data, wherein the user interface apparatus comprises an indication apparatus, in particular a display, in particular a touchscreen display.

The laboratory instrument according to the invention can comprise a plurality of treatment apparatuses. The access control device according to the invention can be assigned to a plurality of laboratory instruments according to the invention, in particular connectable or connected thereto by means of a second interface apparatus and, in particular, second data connections. As a result, one access control device can enable the access of the users to more than one laboratory instrument or to a laboratory instrument with more than one treatment apparatus.

A laboratory instrument according to the invention is preferably capable to work independently, i.e. as a stand-alone instrument, which means it may require some user input but does not require a data connection with a further device, e.g. a central control computer, in order to work in a conventional operating mode. The conventional operating mode of the laboratory instrument provides the treatment of the at least one laboratory sample using its treatment apparatus.

The invention furthermore relates to a method for controlling the access to functions of a laboratory instrument by means of an access control device according to one of claims 1 to 12, wherein the method makes provision, by means of the access apparatus,
a) to log a first requesting user onto the access control device for a session via a first data connection and to assign authorizations and/or access permissions to said user; and
b) during this session, to control the at least one request of at least one further user on the access control device, said request being carried out via a further first data connection and being directed to logging on.

Further possible preferred configurations of the method according to the invention can be derived from the description of the access control device according to the invention and of the laboratory instrument according to the invention and from the preferred configurations thereof.

Further preferred configurations of the access control device according to the invention and of the laboratory instrument according to the invention and of the method according to the invention emerge from the following description of the exemplary embodiments in conjunction with the figures and the description thereof. If nothing else is described or if nothing else emerges from the context, the same components of the exemplary embodiments are substantially characterized by the same reference signs. In detail:

FIG. 1 schematically shows an exemplary embodiment of the access control device according to the invention.

Figure 1:
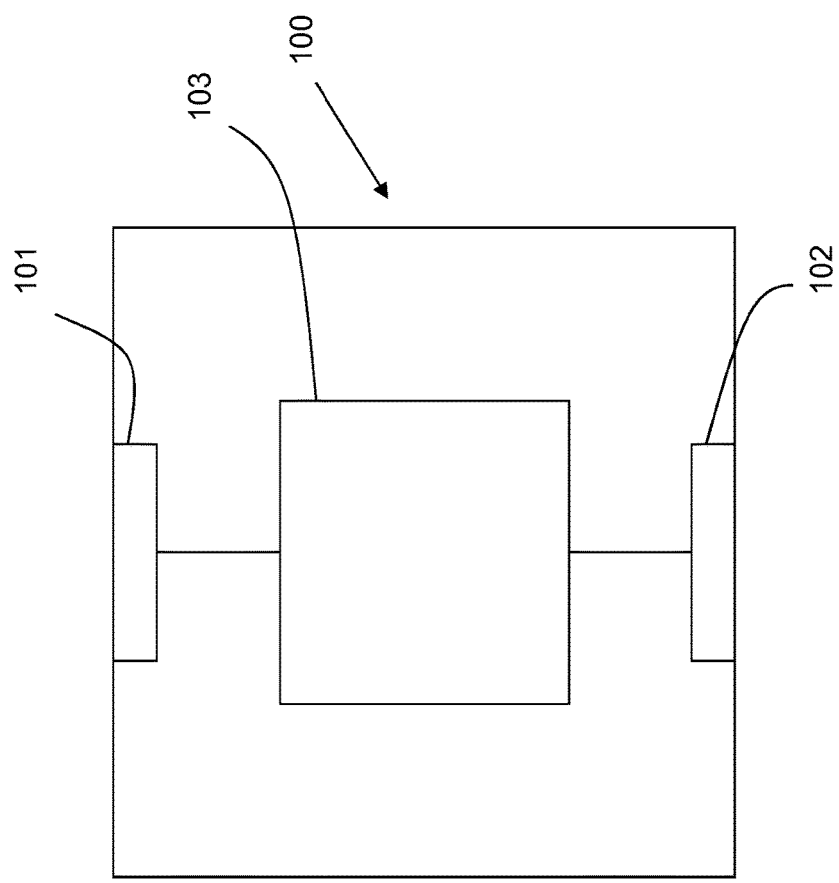

FIG. 1 shows the access control device 100. The access control device 100 is configured for a laboratory instrument which serves for the instrument-controlled treatment of a laboratory sample, in particular for laboratory instruments such as laboratory instrument 1 in FIG. 2a, laboratory instrument 1' in FIG. 4 and laboratory instrument 1" in FIG. 5, wherein the access control device 100 comprises: a first interface apparatus 101 and a second interface apparatus 102; and a control apparatus 103. It is configured a) to establish one or more first data connections to one or more user interface apparatuses via the first interface apparatus; b) to establish a second data connection to the laboratory instrument 1, or alternatively also to 1' or 1", via the second interface apparatus 102; and c) to control authorizations and/or access permissions for the access of users to functions of the laboratory instrument via the first and second data connections. The control apparatus 100 is configured to log a requesting user onto the access control device for a session via a first data connection and to assign him authorizations and/or access permissions and, during this session, to control the at least one request of at least one further user after logging onto the access control device via a further first data connection.

Figure 2B:
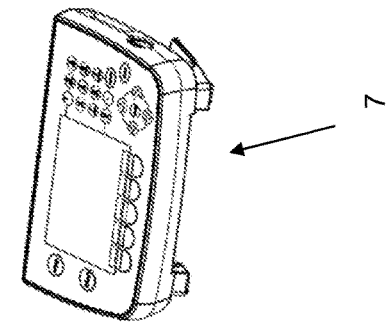
FIG. 2b shows an exemplary embodiment of an external data processing system, by means of which a further user can establish a remote data connection with the access control device of the laboratory instrument from FIG. 2a in order to query a log on at the access control device.
Figure 2A:
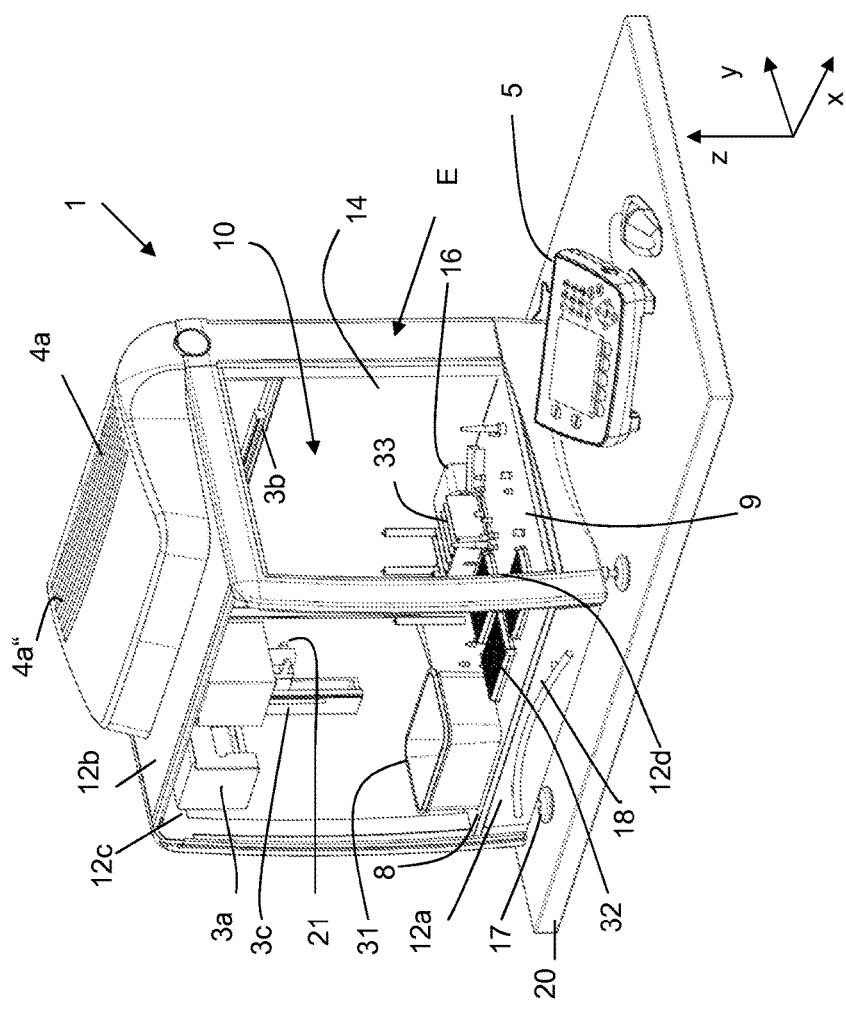
FIG. 2a shows an exemplary embodiment of the laboratory instrument according to the invention, which comprises an access control device according to the invention.

FIG. 2a shows the laboratory instrument 1, which is embodied here as a laboratory machine 1 for treating fluid samples, to be precise as a pipetting machine. The laboratory machine 1 serves for the program-controlled treatment of these samples.

FIG. 2a shows the laboratory machine 1 for automated processing of liquid samples, in particular for the program-controlled treatment of liquid samples. The laboratory machine 1 is a table-top instrument and disposed on the work table 20 with the four feet 17 thereof. It comprises an electronic control apparatus 2 (not shown here), which is suitable for processing program code for the program-controlled treatment of the liquid samples. The control apparatus 2 is attached in the control space, which is denoted by the arrow E and separated from the workspace 10 by a vertical wall 14. The control space also harbours the voltage supply components which supply the suitable supply voltage for the electrical components of the laboratory machine. The control apparatus 103 of the access control device 100 from FIG. 1 is integrated into the control apparatus 2.

The laboratory machine 1 comprises a treatment space 10 for receiving the liquid samples to be treated, a sample handling apparatus 3, controllable in a program-controlled manner, for performing at least one program-controlled treatment step on the at least one sample, which is disposed in the handling space. The components 3a, 3b, 3c and 3d of the movement apparatus are assigned to the sample handling apparatus 3.

The laboratory machine 1 comprises a housing 12 comprising a front side 12a, a rear side 12f (not shown here) disposed opposite to the front side, a top side 12b, a bottom side 12e (not shown here) disposed opposite to the top side and two lateral sides 12c and 12d lying opposite one another. The sides 12a, 12b and 12c are substantially made of a material transparent to visible light.

The front side 12a, which is substantially embodied like a door 12a, namely a sliding door 12a, can be moved by hand and/or moved in a program-controlled manner and can close downward, substantially along the z-axis of the Cartesian coordinate system. FIG. 2a shows the closed position of the door 12a.

The treatment space 10 is delimited by the front side 12a and the two side faces 12c and 12d, as well as the wall 14 and the worktop 8, which forms the upper side of the base plate 9. The worktop 8 provides six handling stations. The handling stations are substantially planar areas in the handling region 8. Pins serve to align the lab-ware, that is to say e.g. the thermorack 33, microtiter plates 32 and waste container 31, at the respective handling station. The exact positioning enables precise, robot-controlled addressing of the sample containers, in particular of the depressions in the microtiter plates 32. A magnetic separation device 16 is disposed in the vicinity of the wall 14, where a thermorack 33, i.e. a temperature-controlled sample vessel holder, is disposed. The magnetic fork (not shown here) of the magnetic separation device 16 enters corresponding receiving channels of the thermorack from the side in order to develop the magnetic effect thereof laterally on the laboratory vessels (sample tubules).

The laboratory machine 1 comprises two decontamination apparatuses, an electronically controllable air purification device for purifying the air in the treatment space, which is controlled electronically and digitally by the control apparatus and which comprises a ventilating device 4a, 4a". The ventilation device comprises three ventilators (not depicted here), which transport an air flow from outside of the device into the treatment space.

The control apparatus 2 comprises a control program. The laboratory machine 1 comprises a sample handling apparatus 3, which comprises a movement apparatus with three guide-rail elements 3a, 3b, 3c, which correspond to movements along the y, x and z-axis of the Cartesian coordinate system. Electronically regulable linear motors are provided for driving the movement along the desired direction. In this manner, the assembly head 21 can be moved into each desired position accessible in the handling space 10. The movement apparatus is part of a robotic system of the sample handling apparatus 3. The assembly head 21 can be transported thereby in a program-controlled manner. A tool instrument, e.g. a pipetting head or a gripper, is connectable to the assembly head. The components disposed in the treatment space, in particular the sample handling apparatus 3, are components of the treatment device of the laboratory machine.

Figure 3:
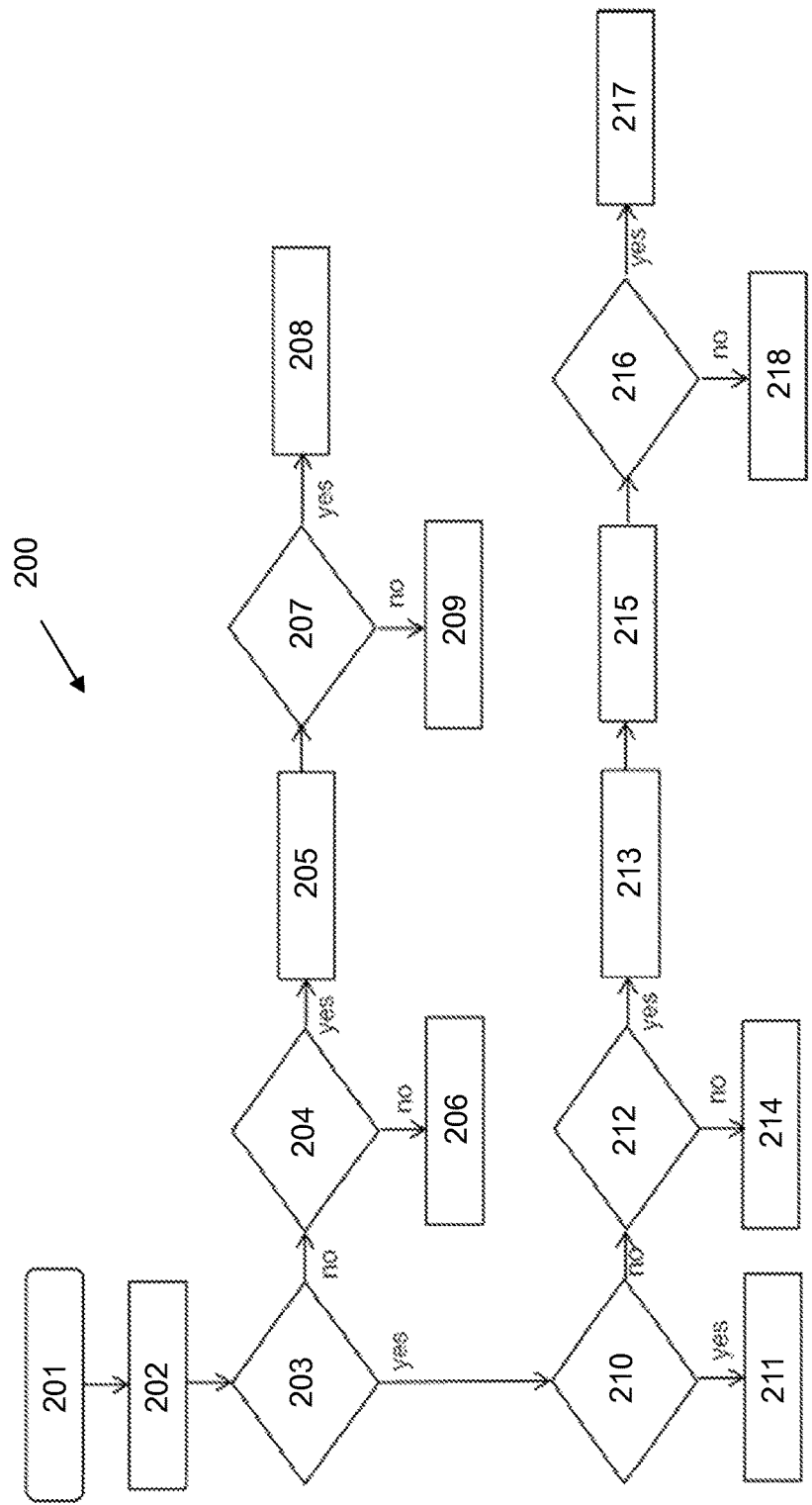
FIG. 3 shows an exemplary embodiment of the method according to the invention for controlling the access of a further user to an access control device of the laboratory instrument in FIG. 2a, on which the session of a first user is active.

The laboratory machine comprises a user interface apparatus 5, by means of which a user can log onto the laboratory machine locally. In the present situation in FIG. 2a, the assumption is made that a first user is logged onto (logged into) the laboratory machine and has started a treatment. The session of the first user is active. In this situation, it is possible that a further user wishes to access the laboratory machine via the mobile user interface apparatus 7 shown in FIG. 2*b*. To this end, he has to log onto the laboratory machine. By way of example, the user interface apparatus 7 can be connectable to the access control device of the laboratory machine by means of a mobile communications connection. FIG. 3 shows an exemplary embodiment of a method 200, by means of which the access control device preferably controls the request of the further user, occurring during the session of the first user, for logging onto the access control device or onto the laboratory machine.

FIG. 3 denotes the further user 201, who carries out a request 202 after logging onto the access control device of the laboratory machine 1, which request occurs during the session of the first user. The authentication preferably takes place in step 202; a specific authorization may, in particular, also already take place in this step; in particular, specific access permissions and/or authorizations can already be granted to or denied from the further user in this step. In particular, it is possible that a second session is already initiated for the further user in step 202, which second session runs parallel to the first session but preferably has different, in particular restricted, access permissions and/or authorizations compared to the session of the first user.

In step 203, the access control device or the control apparatus thereof preferably checks whether the treatment apparatus of the laboratory machine is running, i.e. whether it is active. Alternatively, it would also be possible for a check as to whether a session of a first user is running, i.e. whether a first user is logged on, only to be carried out in step 203. If the check in step 203 is answered "yes", a check is carried out in step 210 as to whether the first, already logged on user is identical to the further user 201. This is possible since both users were uniquely established using the authentication data thereof and therefore can be distinguishable as a matter of principle.

If the access control device determines that the further user is not identical to the first user, the further user is preferably denied access to the function of the control device of the treatment apparatus by virtue of said user not being granted the access permissions and/or authorizations required for this (step 211). It would also be possible and preferred for the further user to be denied all access permissions and/or authorizations in step 211, i.e. that there is no authorization for the further user.

In step 210, the access control device can also conclude that the further user is identical to the first user. Then, in step 212, the access control device can check whether the access of the further user—the identity of which then corresponds to that of the first user—occurs over a different user interface apparatus than in the case of the access or logging on of the first user. The information about the identity of the user interface apparatus can be stored in the access control device or in the laboratory instrument during access or during authentication of a user. If the users are different, the authorization may take place (step 214). If the users are identical, a synchronization process can be initiated.

The synchronization process can lead to the user interface by means of which the second (the further) access occurs being put into the state in which the first user interface apparatus, by means of which the first access or the first authorization, earlier in time, took place, was as well. This state can be at least in such a way that work can continue on the second user interface apparatus in the same manner as on the first user interface apparatus, in particular that the current session of the first user can be continued using the second user interface apparatus.

The synchronization process can provide for parameters to be synchronized (step 213) and for a priority being requested for the second user interface apparatus (step 215). What this means is that the access control device can make a decision on the basis of optional further criteria whether, given an identity of the users, access to the laboratory machine or the treatment apparatus thereof is in fact granted (step 217) or not (step 218) via the second use interface apparatus.

In the case of the check in step 203, the access control device may conclude that the treatment apparatus of the laboratory machine is not running, i.e. it is inactive. Alternatively, it would also be possible to determine in step 203 that no session of a first user is running, i.e. no first user is logged on. In the case of these results, a check can be carried out in step 204 as to whether a first user is logged on and has the access permissions and/or authorizations for controlling the treatment apparatus. Alternatively, the check carried out in step 204 only concerns whether a first user is logged on, i.e. has any access permissions and/or authorizations. If the check in step 204 results in a "no", there can be an authorization (for controlling the treatment apparatus or, alternatively, for logging on/authorizing) (step 206). If the check in step 204 results in a "yes", there can be a request in step 205 during the logging-on process of the further user to the extent that the first user loses permissions which the further user requires for the desired authorization. If the check of this request in step 207 results in the permission transfer not being permissible as a result of any criterion used by the access control device, it does not occur (step 209), otherwise it does occur (step 208).

Figure 4:
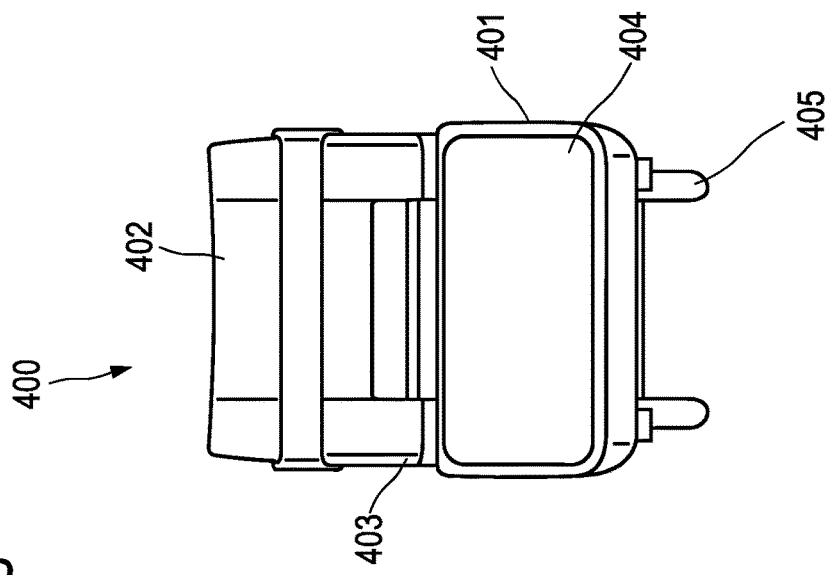
FIG. 4 shows a further exemplary embodiment of the laboratory instrument according to the invention, in this case a thermocycler.

FIG. 4 shows a laboratory instrument 400, a thermocycler, embodied for automated processing of liquid samples, in particular for the program-controlled temperature control of liquid samples. The laboratory instrument 400 is a tabletop instrument. It comprises an integrated electronic control apparatus 406 (not shown here), which is suitable for processing program code for the program-controlled treatment of the liquid samples. The control apparatus 406 is housed in the housing 401. The housing also harbours the voltage supply components which supply the suitable supply voltage for the electrical components of the thermocycler.

The laboratory instrument 400 comprises a treatment space 403 for receiving the liquid samples to be treated, which can hold at least one treatment apparatus 408 (not shown here), controllable in a program-controlled manner, for performing at least one program-controlled treatment step on the at least one sample, which is disposed in the treatment apparatus disposed in the handling space. The treatment space can be sealed by a cover 402 in order to establish defined temperature-control surroundings. In FIG. 4, the laboratory instrument is depicted in the closed state.

The control apparatus 103 of the access control device 100 from FIG. 1 is integrated into the control apparatus 406. The control apparatus 406 comprises a control program.

The laboratory instrument comprises a user interface apparatus 404, by means of which a user can log onto the laboratory instrument locally. In the present situation in FIG. 4, the assumption is made that a first user is logged onto (logged into) the laboratory machine and has started a treatment. The session of the first user is active. In this situation, it is possible that a further user wishes to access the laboratory instrument via the mobile user interface apparatus 7 shown in FIG. 2*b*. To this end, he has to log onto the laboratory instrument. By way of example, the user interface apparatus 7 can be connectable to the access control device of the laboratory instrument by means of a mobile communications connection. An exemplary embodiment is depicted in FIG. 3.

Figure 5:
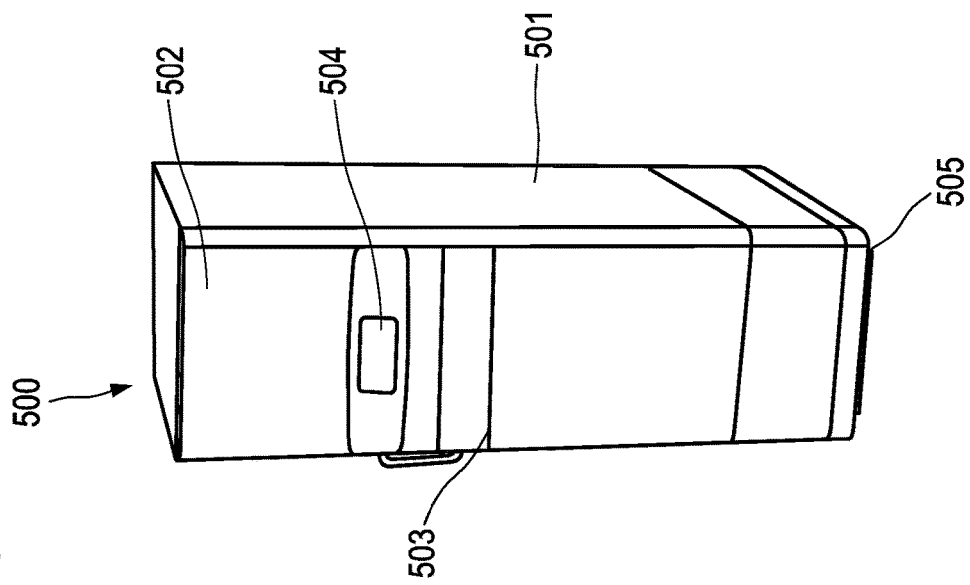
FIG. 5 shows a further exemplary embodiment of the laboratory instrument according to the invention, in this case a laboratory freezer.

FIG. 5 shows, in a further exemplary embodiment of the invention, a laboratory instrument 500, a laboratory freezer, for storing laboratory samples, in particular at temperatures under −50° C. The laboratory instrument 500 is a tabletop instrument. It comprises an integrated electronic control apparatus 506 (not shown here), which is suitable for setting, regulating and monitoring the temperature in the required range. The control apparatus 506 is housed in the housing 501. The housing also harbours the voltage supply components which supply the suitable supply voltage for the electrical components of the laboratory freezer.

The laboratory instrument 500 comprises a treatment space 503 for holding the samples to be stored, comprising at least one program-controlled controllable treatment apparatus 408 (not shown here) which, in the case of the laboratory freezer, corresponds to a sealed region with a defined adjustable temperature. Here, the program-controlled treatment step corresponds to freezing the at least one sample, which is disposed in the treatment apparatus disposed in the handling space. The treatment space can be sealed by a door 502 in order to establish defined temperature-control surroundings. In the case of more than one treatment apparatus, a plurality of doors, optionally disposed behind the common door 502, are also conceivable. In FIG. 5, the laboratory instrument is depicted in the closed state.

The control apparatus 103 of the access control device 100 from FIG. 1 is integrated into the control apparatus 506 of the laboratory instrument 500. The control apparatus 406 comprises a control program.

The laboratory instrument comprises a user interface apparatus 504, by means of which a user can log onto the laboratory instrument locally. In the present situation in FIG. 5, the assumption is made that a first user is logged onto (logged into) the laboratory machine. The treatment is started and runs permanently. The session of the first user is active. In this situation, it is possible that a further user wishes to access the laboratory instrument via the mobile user interface apparatus 7 shown in FIG. 2b. To this end, he has to log onto the laboratory instrument. By way of example, the user interface apparatus 7 can be connectable to the access control device of the laboratory instrument by means of a mobile communications connection. An exemplary embodiment is depicted in FIG. 3.

APPENDIX 1

Possible Program Parameters as a Function of the Laboratory Instrument Type

| Instrument | Most important parameter | | | | | Sequence programming |
|---|---|---|---|---|---|---|
| Centrifuge | Temperature | Speed | | Time | | No, steps conceivable |
| Cycler | Temperature | | | Time | | Steps |
| Biospectrometer | Temperature (kinetic) | | | | Result | Complex process |
| Plate reader | Temperature | Sample number | | | Result | Complex process |
| Cell counter | | | | | Result | Complex process |
| Incubator | Temperature | CO2/O2 | Relative humidity | Time | | No, steps conceivable |
| Shaker | Temperature | Speed | | | | Steps |
| Freezer | Temperature | Alarm value | | | | No |
| Fermenter/bioreactor | | Stirrer rotational speed | Dissolved oxygen (DO) | pH | Metering speed (pumps) | |
| Laboratory machine | Sample number | Sample volume | Pipetting tools | Source/Target | Transfer type (pipetting/dispensing) | Complex process |
| (Thermal) mixer | Temperature | Speed | | Time | | Restricted steps |
| Pipetting control device | Sample volume | | Pipetting tools | | Transfer type | Restricted steps |
| Biosafety cabinet | | Flow speed | Filter service life | Ventilator service life | Amount of air | |

| | | |
|---|---|---|
| Use cases to be considered (examples): | Remote monitoring | |
| | Remote control | |
| | Booking schedule | |
| | Service access | |
| | Pre-programming | |
| Roles to be considered (examples): | Admin | |
| | LabUser | |
| | Inexperienced | |
| | Manager | |
| | Service | |
| Instruments to be considered (examples): | Cycler | n treatment apparatuses (thermoblocks) |
| Assumption: Access permissions are independent of the instrument | Centrifuge | 1 treatment apparatus (rotor) |
| | Shaker | 1 treatment apparatus (shaker platform, a plurality thereof also conceivable) |
| | Incubator | 1 treatment apparatus |
| | Cell counter | 1 treatment apparatus |
| | BSC | 1 treatment apparatus |
| | Freezer | n treatment apparatuses conceivable (differently actuatable cooling levels) |
| | Laboratory machine | 1 treatment apparatus |
| | Biospectrometer | 1 treatment apparatus |

Use case: Remote monitoring

| State | Role logged in | Access possible? |
|---|---|---|
| *User: Admin* | | |
| Idle (ready) | Admin | Y |
|  | LabUser | Y |
|  | Inexperienced | Y |
|  | Manager | Y |
| Programmed =idle? | Admin | Y |
|  | LabUser | Y |
|  | Inexperienced | Y |
|  | Manager | Y |
| Started (running) | Admin | Y |
|  | LabUser | Y |
|  | Inexperienced | Y |
|  | Manager | Y |
| Stopped (finished) =idle? | Admin | Y |
|  | LabUser | Y |
|  | Inexperienced | Y |
|  | Manager | Y |
| Booking =idle? | Admin | Y |
|  | LabUser | Y |
|  | Inexperienced | Y |
|  | Manager | Y |
| Standby | — | Y |

Use case: Remote monitoring

| State | Role logged in | Access possible? |
|---|---|---|
| *User: LabUser* | | |
| Idle (ready) | Admin | Y |
|  | LabUser | Y |
|  | Inexperienced | Y |
|  | Manager | Y |
| Programmed = idle? | Admin | Y |
|  | LabUser | Y |
|  | Inexperienced | Y |
|  | Manager | Y |
| Started (running) | Admin | Y |
|  | LabUser | Y |
|  | Inexperienced | Y |
|  | Manager | Y |
| Stopped (finished) = idle? | Admin | Y |
|  | LabUser | Y |
|  | Inexperienced | Y |
|  | Manager | Y |
| Standby | — | Y |

Use case: Remote monitoring

| State | Role logged in | Access possible? |
|---|---|---|
| *User: Inexperienced* | | |
| Idle (ready) | Admin | N |
|  | LabUser | N |
|  | Inexperienced | N |
|  | Manager | N |
| Programmed = idle? | Admin | N |
|  | LabUser | N |
|  | Inexperienced | N |
|  | Manager | N |
| Started (running) | Admin | N |
|  | LabUser | N |
|  | Inexperienced | N |
|  | Manager | N |
| Stopped (finished) = idle? | Admin | N |
|  | LabUser | N |
|  | Inexperienced | N |
|  | Manager | N |
| Standby | — | Y |

| State | Role logged in | Access possible? |
|---|---|---|
| *User: Manager* | | |
| Idle (ready) | Admin | Y |
|  | LabUser | Y |
|  | Inexperienced | Y |
|  | Manager | Y |
| Programmed = idle? | Admin | Y |
|  | LabUser | Y |
|  | Inexperienced | Y |
|  | Manager | Y |
| Started (running) | Admin | Y |
|  | LabUser | Y |
|  | Inexperienced | Y |
|  | Manager | Y |
| Stopped (finished) = idle? | Admin | Y |
|  | LabUser | Y |
|  | Inexperienced | Y |
|  | Manager | Y |
| Standby | — | Y |

Use case: Remote control

| State | Role logged in | Access possible? |
|---|---|---|
| *User: Admin* | | |
| Idle (ready) | Admin | N |
|  | LabUser | Y |
|  | Inexperienced | Y |
|  | Manager | Y |
| Programmed = idle? | Admin | N |
|  | LabUser | Y |
|  | Inexperienced | Y |
|  | Manager | Y |
| Started (running) | Admin | N |
|  | LabUser | Y |
|  | Inexperienced | Y |
|  | Manager | Y |
| Stopped (finished) = idle? | Admin | N |
|  | LabUser | Y |
|  | Inexperienced | Y |
|  | Manager | Y |
| Booking = idle? | Admin | N |
|  | LabUser | Y |
|  | Inexperienced | Y |
|  | Manager | Y |
| Standby | — | N |

Use case: Remote control

| State | Role logged in | Access possible? |
|---|---|---|
| *User: LabUser* | | |
| Idle (ready) | Admin | N |
|  | LabUser | N |
|  | Inexperienced | Y |
|  | Manager | N |
| Programmed = idle? | Admin | N |
|  | LabUser | N |
|  | Inexperienced | Y |
|  | Manager | N |
| Started (running) | Admin | N |
|  | LabUser | N |
|  | Inexperienced | Y |
|  | Manager | N |
| Stopped (finished) = idle? | Admin | N |
|  | LabUser | N |
|  | Inexperienced | Y |
|  | Manager | N |

-continued

| State | Role logged in | Access possible? |
|---|---|---|
| Booking = idle? | Admin | N |
| | LabUser | N |
| | Inexperienced | Y |
| | Manager | N |
| Standby | — | N |

Use case: Remote control

| State | Role logged in | Access possible? |
|---|---|---|
| User: Inexperienced | | |
| Idle (ready) | Admin | N |
| | LabUser | N |
| | Inexperienced | N |
| | Manager | N |
| Programmed = idle? | Admin | N |
| | LabUser | N |
| | Inexperienced | N |
| | Manager | N |
| Started (running) | Admin | N |
| | LabUser | N |
| | Inexperienced | N |
| | Manager | N |
| Stopped (finished) = idle? | Admin | N |
| | LabUser | N |
| | Inexperienced | N |
| | Manager | N |
| Booking = idle? | Admin | N |
| | LabUser | N |
| | Inexperienced | N |
| | Manager | N |
| Standby | — | N |

Use case: Remote control

| State | Role logged in | Access possible? |
|---|---|---|
| User: Manager | | |
| Idle (ready) | Admin | N |
| | LabUser | Y |
| | Inexperienced | N |
| | Manager | N |
| Programmed = idle? | Admin | N |
| | LabUser | Y |
| | Inexperienced | N |
| | Manager | N |
| Started (running) | Admin | N |
| | LabUser | Y |
| | Inexperienced | N |
| | Manager | N |
| Stopped (finished) = idle? | Admin | N |
| | LabUser | Y |
| | Inexperienced | N |
| | Manager | N |
| Booking = idle? | Admin | N |
| | LabUser | Y |
| | Inexperienced | N |
| | Manager | N |
| Standby | — | N |

Use case: Booking schedule

| State | Role logged in | Access possible? |
|---|---|---|
| User: Admin | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use case: Booking schedule

| State | Role logged in | Access possible? |
|---|---|---|
| User: LabUser | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use case: Booking schedule

| State | Role logged in | Access possible? |
|---|---|---|
| User: Inexperienced | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |

-continued

| State | Role logged in | Access possible? |
|---|---|---|
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use case: Booking schedule

| State | Role logged in | Access possible? |
|---|---|---|
| User: Manager | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | N |
| | LabUser | N |
| | Inexperienced | N |
| | Manager | N |
| Standby | — | Y |

Use case: Pre-programming

| State | Role logged in | Access possible? |
|---|---|---|
| User: Admin | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use case: Pre-programming

| State | Role logged in | Access possible? |
|---|---|---|
| User: LabUser | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use case: Pre-programming

| State | Role logged in | Access possible? |
|---|---|---|
| User: Inexperienced | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use case: Pre-programming

| State | Role logged in | Access possible? |
|---|---|---|
| User: Manager | | |
| Idle (ready) | Admin | Y |
| | LabUser | Y |
| | Inexperienced | Y |
| | Manager | Y |
| Programmed = idle? | Admin | Y |
| | LabUser | Y |
| | Inexperienced | Y |
| | Manager | Y |
| Started (running) | Admin | Y |
| | LabUser | Y |
| | Inexperienced | Y |
| | Manager | Y |

-continued

| State | Role logged in | Access possible? |
|---|---|---|
| Stopped (finished) = idle? | Admin | Y |
| | LabUser | Y |
| | Inexperienced | Y |
| | Manager | Y |
| Booking = idle? | Admin | Y |
| | LabUser | Y |
| | Inexperienced | Y |
| | Manager | Y |
| Standby | — | Y |

Use case: Remote service access

| State | Role logged in | Access possible? |
|---|---|---|
| User: Service | | |
| Idle (ready) | Admin | Y |
| | LabUser | N |
| | Inexperienced | N |
| | Manager | Y |
| Programmed = idle? | Admin | Y |
| | LabUser | N |
| | Inexperienced | N |
| | Manager | Y |
| Started (running) | Admin | Y |
| | LabUser | N |
| | Inexperienced | N |
| | Manager | Y |
| Stopped (finished) = idle? | Admin | Y |
| | LabUser | N |
| | Inexperienced | N |
| | Manager | Y |
| Booking = idle? | Admin | Y |
| | LabUser | N |
| | Inexperienced | N |
| | Manager | Y |
| Standby | — | Y |

The invention claimed is:

1. A laboratory instrument for the instrument-controlled treatment of at least one laboratory sample, the laboratory instrument being selected from the group of laboratory instruments consisting of: a centrifuge, a thermocycler, a biospectrometer, a cell counter, an incubator, a laboratory shaker, a laboratory mixer, a laboratory freezer, a bioreactor, a safety work bench, a biological safety cabinet, a sample plate reader, and a laboratory machine for treating fluid samples; the laboratory instrument comprising:
   at least one treatment apparatus for performing the treatment of the at least one laboratory sample,
   a control apparatus of the laboratory instrument, having a data processing apparatus, for controlling the instrument-controlled treatment of the at least one laboratory sample, and
   a housing, which houses the at least one treatment apparatus;
   a first user interface apparatus;
   an access control device, the access control device being integrated into the laboratory instrument and comprising:
   a first interface apparatus and a second interface apparatus; and
   a control apparatus of the access control device;
   the control apparatus of the laboratory instrument and the access control device being housed within said housing;
   wherein the control apparatus of the access control device is programmed to perform the following steps:
   a) establishing one or more first data connections to the first user interface apparatus or more user interface apparatuses via the first interface apparatus;
   b) establishing a second data connection to the control apparatus of the laboratory instrument via the second interface apparatus; and
   c) controlling authorizations and/or access permissions for user access to functions of the laboratory instrument via the first and second data connections;
   wherein the control apparatus of the access control device is programmed to control the authorizations and/or access permissions in such a way that there is simultaneous access by the first and at least one further user within each case separately assigned authorizations and/or access permissions to functions of the laboratory instrument,
   the control apparatus of the access control device is programmed to perform the following steps: logging a first user requesting a first session on a laboratory instrument via a first data connection onto the access control device and assigning said user authorizations and/or access permissions, wherein the function of the laboratory instrument performed in accordance with the authorizations and/or access permissions of the first user contains the treatment of the at least one laboratory sample by the at least one treatment apparatus, and
   the control apparatus of the access control device is programmed to perform the following step, during this session: controlling the at least one request of at least one further user on the access control device, said request being carried out via a further first data connection and being directed to logging on.

2. The laboratory instrument according to claim 1, wherein the control apparatus of the access control device is programmed to perform the following steps, during the session of the first user: logging the at least one further requesting user onto the access control device and starting a session for this further user, said session occurring parallel to the session of the first user for at least some of the time.

3. The laboratory instrument according to claim 1 or 2, wherein the control apparatus of the access control device is programmed to perform the following step: assigning, in any case after the at least one further requesting user has logged on, authorizations and/or access permissions to said at least one further requesting user during the session of the first user.

4. The laboratory instrument according to claim 1, wherein the control apparatus of the access control device is programmed in such a way that, when a first user has activated one or more functions of the laboratory instrument, the authorizations and/or access permissions of each further logged-on user are set in such a way that the performance of an already activated function of the laboratory instrument cannot be influenced by an activation of a function permitted in accordance with the authorizations and/or access permissions of the further user.

5. The laboratory instrument according to claim 1, wherein the control apparatus of the access control device is programmed in such a way that the authorizations and/or access permissions of the first user or of each further user are set as a function of the operating state of the laboratory instrument.

6. The laboratory instrument according to claim 1, wherein the first interface apparatus enables logging on and accessing functions of the laboratory instrument via at least two different user interface apparatuses and wherein control apparatus of the access control device is configured in such a way that, in the case of logging on via a second user interface apparatus, a check is carried out as to whether the logging-on user has already in advance, via a first user interface apparatus,
a) activated one or more of the currently performed functions of the laboratory instrument or
b) is already logged on, and,
if condition a) or b) is satisfied, the authorizations and/or access permissions assigned to the user during the preceding log on by the access control device via the first user interface apparatus are assigned for access to the laboratory instrument via the second user interface apparatus.

7. The laboratory instrument according to claim 6, wherein the control apparatus of the access control device is programmed in such a way that an additional check is carried out as to whether at least one further predetermined condition is satisfied during the log on at the second user interface apparatus and the access permissions for access to the laboratory instrument via the second user interface apparatus are only assigned if the at least one further predetermined condition is also satisfied.

8. The laboratory instrument according to claim 7, wherein the control apparatus of the access control device is programmed in such a way that, if a) or b) is satisfied, information about the operating state of the laboratory instrument, measured values or settings and programs of the laboratory instrument which can be influenced by users are transmitted to the second user interface apparatus via the interface apparatus.

9. The laboratory instrument according to claim 1, which comprises a communication apparatus for establishing a remote data connection for data interchange with an external instrument, which likewise comprises a suitable communication apparatus for establishing a remote connection for data interchange with the laboratory machine.

10. A method for controlling the access to functions of a laboratory instrument according to claim 1, wherein the method makes provision
a) to establish one or more first data connections to one or more user interface apparatuses via the first interface apparatus;
b) to establish a second data connection to the laboratory instrument via the second interface apparatus; and
c) to control authorizations and/or access permissions for user access to functions of the laboratory instrument via the first and second data connections;
wherein the control apparatus is configured to log a first requesting user onto the access control device for a session via a first data connection and to assign authorizations and/or access permissions to said user and
the access control device is configured, during this session, to control the at least one request of at least one further user on the access control device, said request being carried out via a further first data connection and being directed to logging on.

11. The laboratory instrument according to claim 1, wherein the control apparatus of the access control device is programmed to allow, when at least one condition is present, an amendment of the authorizations and/or access permissions in such a way that a further user at least partially obtains the authorizations and/or access permissions of the first user instead of said first user.

12. The laboratory instrument according to claim 11, wherein the control apparatus of the access control device is programmed in such a way that the authorizations and/or access permissions obtained by the further user instead of the first user contain the permission for controlling the treatment apparatus.

13. The laboratory instrument according to claim 12, wherein the control apparatus of the access control device is programmed in such a way that the function performed in accordance with the authorizations and/or access permissions of the first user contains the treatment of the at least one sample by a treatment apparatus of the laboratory instrument.

14. The laboratory instrument according to claim 1, wherein the first user interface apparatus is provided separately from the laboratory instrument and is connected for a user data input to the control apparatus of the laboratory instrument and/or to the control apparatus of the access control device.

* * * * *